United States Patent [19]
McEwan

[11] Patent Number: 5,361,070
[45] Date of Patent: Nov. 1, 1994

[54] ULTRA-WIDEBAND RADAR MOTION SENSOR

[75] Inventor: Thomas E. McEwan, Livermore, Calif.

[73] Assignee: Regents of the University of California, Oakland, Calif.

[21] Appl. No.: 44,717

[22] Filed: Apr. 12, 1993

[51] Int. Cl.$^5$ ............................................. G01S 13/00
[52] U.S. Cl. ................................................. 342/21
[58] Field of Search ................................. 342/28, 21

[56] References Cited

U.S. PATENT DOCUMENTS 3,686,669 8/1972 Toulis .
3,772,697 11/1973 Ross .
4,150,375 4/1979 Ross et al. ............................... 342/21
5,148,174 9/1992 Harmuth ................................. 342/21

Primary Examiner—Mark Hellner
Attorney, Agent, or Firm—Henry P. Sartorio

[57] ABSTRACT

A motion sensor is based on ultra-wideband (UWB) radar. UWB radar range is determined by a pulse-echo interval. For motion detection, the sensors operate by staring at a fixed range and then sensing any change in the averaged radar reflectivity at that range. A sampling gate is opened at a fixed delay after the emission of a transmit pulse. The resultant sampling gate output is averaged over repeated pulses. Changes in the averaged sampling gate output represent changes in the radar reflectivity at a particular range, and thus motion.

20 Claims, 12 Drawing Sheets

ULTRA-WIDEBAND RADAR MOTION SENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The invention relates generally to motion sensors and more particularly to motion sensors based on ultra-wideband radar.

Motion sensors are primarily based on ultrasound, passive infrared (PIR) and radar detectors. Ultrasonic motion sensors are commonly used for automatic door openers and security alarms. They are of low cost and can operate with narrow beamwidths. However, installation options are limited since ultrasonic beams are easily blocked by thin materials, including paper. Another short-coming is the tendency to false trigger on reflections from blowing curtains or flying insects.

PIR sensors are perhaps the most frequently used home security sensor. They use a special Fresnel lens to generate multiple thermal images of a warm object, such as a person. As the person traverses the field of view, the thermal images produce periodic fluctuations as they sweep across an IR sensor element, which are then detected by low cost electronics. As with ultrasound, PIR can be blocked by a sheet of paper. Furthermore, PIR has no range adjustment.

FM-CW radar sensors emit a swept frequency microwave signal and compare the frequency of the echo with its current emission frequency, producing a beat frequency proportional to range. FM-CW radar sensors use low cost microwave oscillators and detector diodes, and audio frequency processing electronics to determine the audio beat frequency, or range. Nonranging radar sensors simply emit a continuous microwave carrier and listen for a Doppler shift from a moving object. The antennas are usually low cost, die cast metal horns. The main limitations to FM-CW and Doppler radar are:
1) limited materials penetration due to the high microwave frequencies employed,
2) microphonics caused by the use of short radar wavelengths combined with audio frequency processing,
3) frequency crowding, and
4) poor short-range operation. Short range performance is limited by close-in noise sidebands in the transmit oscillator, which must operate in the gigahertz region and yet not have random frequency variations on the order of 100 Hz, since this variation would be indistinguishable from the desired beat frequencies.

SUMMARY OF THE INVENTION

Ultra-wideband (UWB) radar motion sensing is a completely new approach to motion sensor technology. UWB radar operates as a pulse-echo system that clocks the two-way time of flight of a very short electrical pulse. A carrier frequency is not used; instead, an electrical voltage pulse is applied directly to the antenna.

Since frequency up-conversion by a modulator is not used, there is no frequency to tune in. The UWB transmit spectrum is the Fourier transform of the emitted pulse and generally spans hundreds of megaHertz to several gigaHertz. It is inherently spread-spectrum. A frequency allocation by the FCC is not relevant. Furthermore, many independent UWB sensors may be co-located without interference.

By not using frequency up-conversion, the UWB spectrum is located as close to DC as possible. Since most materials exhibit rapidly increasing attenuation with frequency, UWB radar has a very significant advantage in materials penetration. Tests show that 200 ps pulses freely penetrate gypsum, wood, and concrete walls. Excellent materials penetration is a fundamental advantage to UWB sensors, and will allow their installation behind walls and appliance panels, above ceilings and below floors.

UWB radar range is determined by the pulse-echo interval. For motion detection, the sensors operate by staring at a fixed range and then sensing any change in the averaged radar reflectivity at that range. This is accomplished by opening a sampling gate at a fixed delay after the emission of the transmit pulse, and then averaging the resultant sampling gate output over repeated pulses. Changes in the averaged sampling gate output represent changes in the radar reflectivity at a particular range, and thus motion.

An invisible, constant-range spherical shell is effectively projected into space, the thickness of which is directly related to the radar pulse width. In two illustrative embodiments, one sensor has a shell thickness of one inch, and the other about 18 inches.

The location of the detection shell is set by adjusting the sampling gate delay. This delay adjustment is easily implemented, and can be adjusted down to point blank range with no performance penalty. User adjustable detection range is another outstanding feature of UWB sensors.

The cost of UWB motion sensors will be on a par with competing sensors, so its selection as the most appropriate sensor technology for many applications will be assured. Near term UWB sensors will be built with off-the-shelf components. Eventually, a silicon, application specific integrated circuit (ASIC) may embody all the sensor electronics.

UWB motion sensor electronics may also be connected to electro-optical transducers, such as light emitting diodes and PIN photodiodes to project the detection shell optically. This would be particularly useful where pencil beam sensing, i.e., "light saber" operation is desired.

DETAILED DESCRIPTION OF THE PREFERRED EMBODIMENTS

Figure 1:
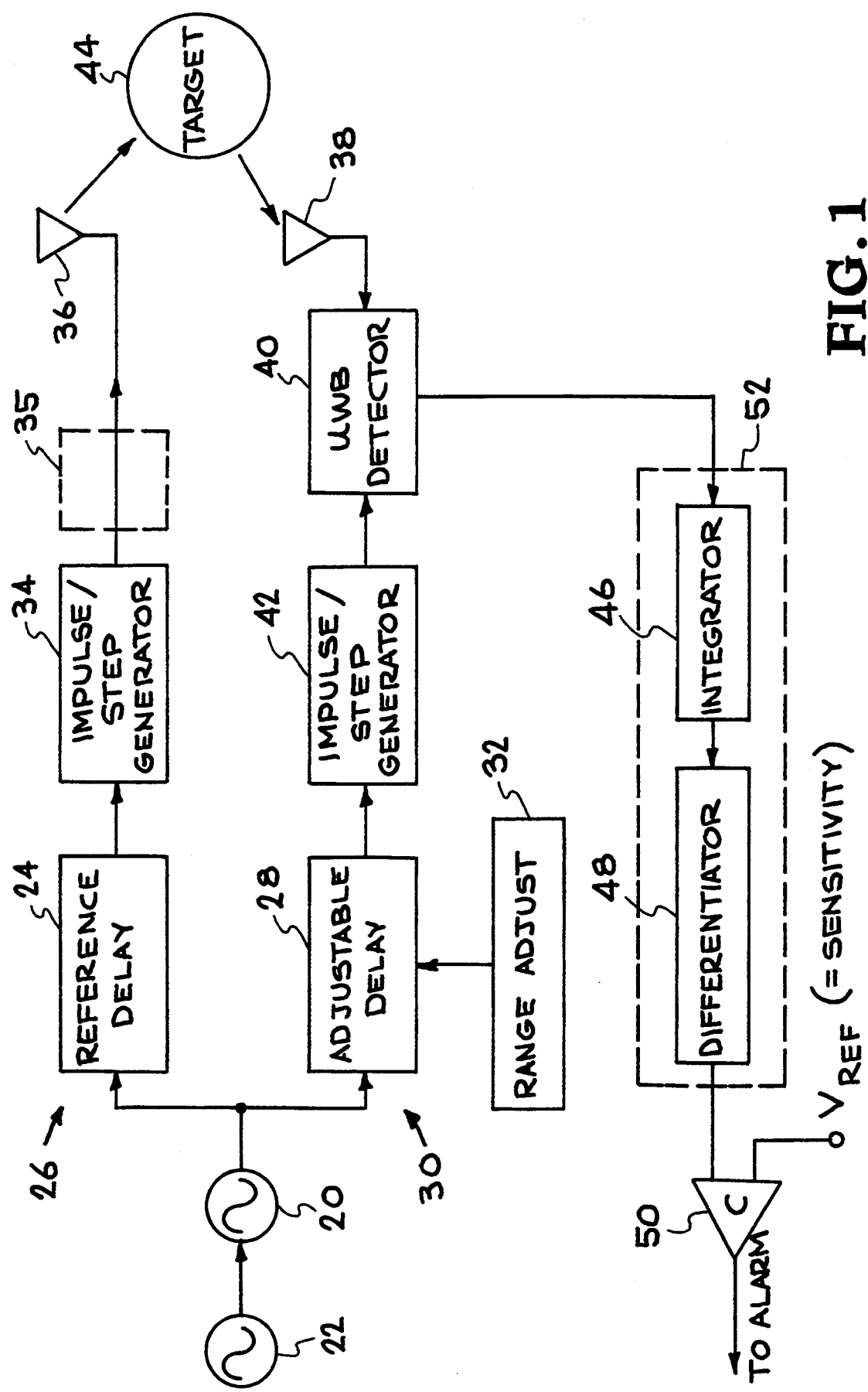
FIG. 1 is a block diagram of a UWB radar motion sensor.

Referring to FIG. 1, a free-running oscillator (PRI generator) 20 generates the radar pulse repetition interval (PRI). Typically, this interval is 1 μs. A noise generator 22 is connected to the PRI generator 20 to introduce a random variation to the PRI, for purposes to be described below. The output of the PRI generator 20 drives two delay means, a fixed reference delay means 24 in the transmit path 26, and an adjustable delay means 28 in the receive (gating pulse) path 30. Delay means 28 is adjusted by range adjustment means 32.

The reference delay means 24 is generally set to match the minimum delay in the receive path 30, and may also be set to account for delays in the antenna feed lines, etc. The output of the reference delay means 24 drives an impulse (or step) generator 34 which provides the transmit pulse. If PRI generator 20 or reference delay means 24 produce a pulse with sufficiently fast rise time, then impulse (or step) generator 34 may be omitted. Otherwise, generator 34 is used to generate a suitable transmit pulse. The transmit pulse typically resembles a Gaussian shaped voltage pulse. In general, it is not a modulated RF pulse. The UWB radar differs from conventional radar in that no carrier frequency is used. Rather, a sequence of individual pulses, spaced by the PRI, is applied directly to the antenna.

The transmit pulse is directly radiated by the transmit antenna 36. There are several UWB antennas in common use, the most common of which is the tapered slot antenna, also known as an endfire antenna. In preferred embodiments, both simple wire dipoles and broader band "bow-tie" dipoles are used. Due to their resonant nature, ringing is produced in the emitted radiation, but this effect is put to use, as will be described below.

Figure 5:
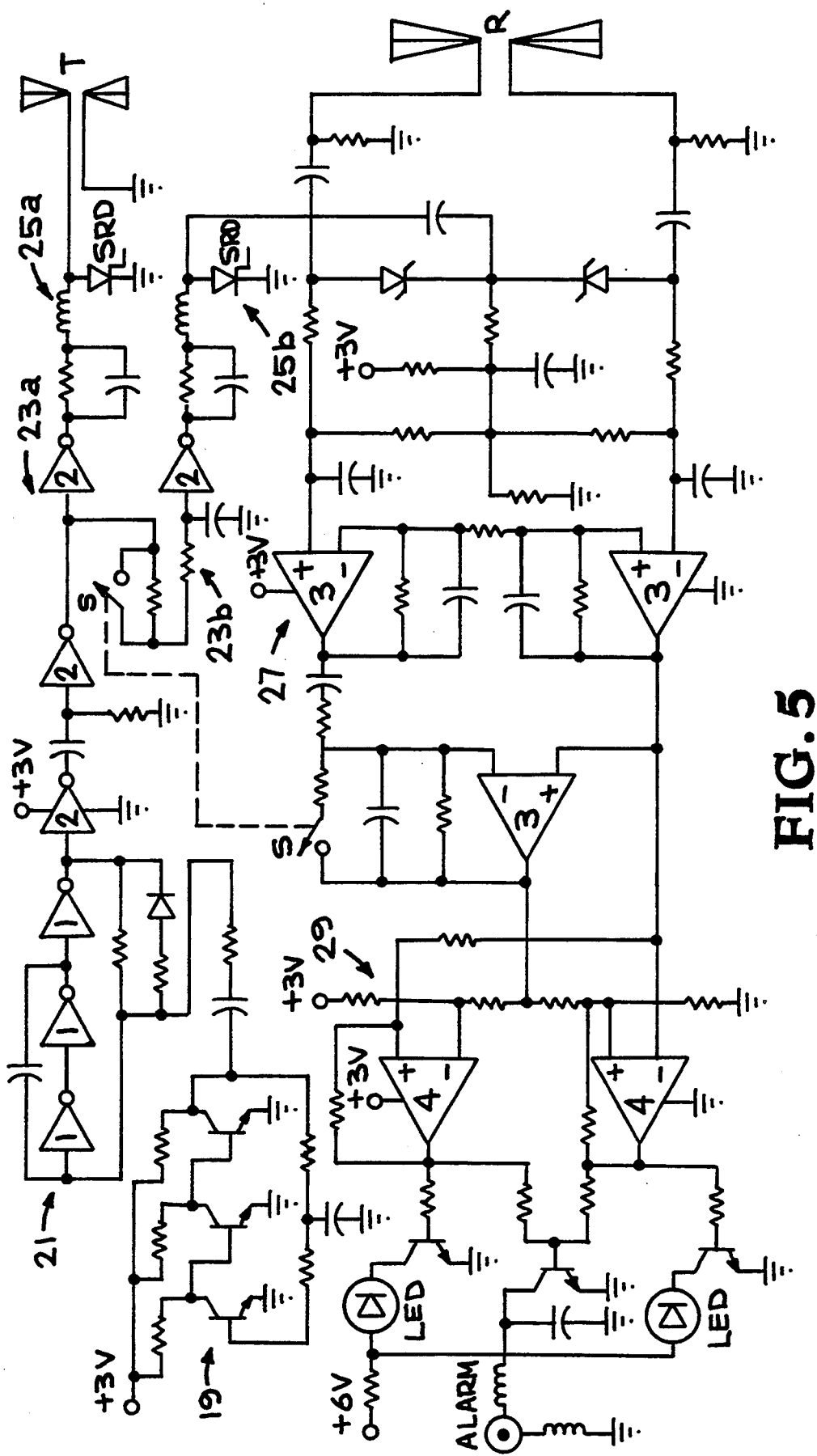
FIG. 5 is a schematic diagram of a UWB radar motion sensor.
Figure 6:
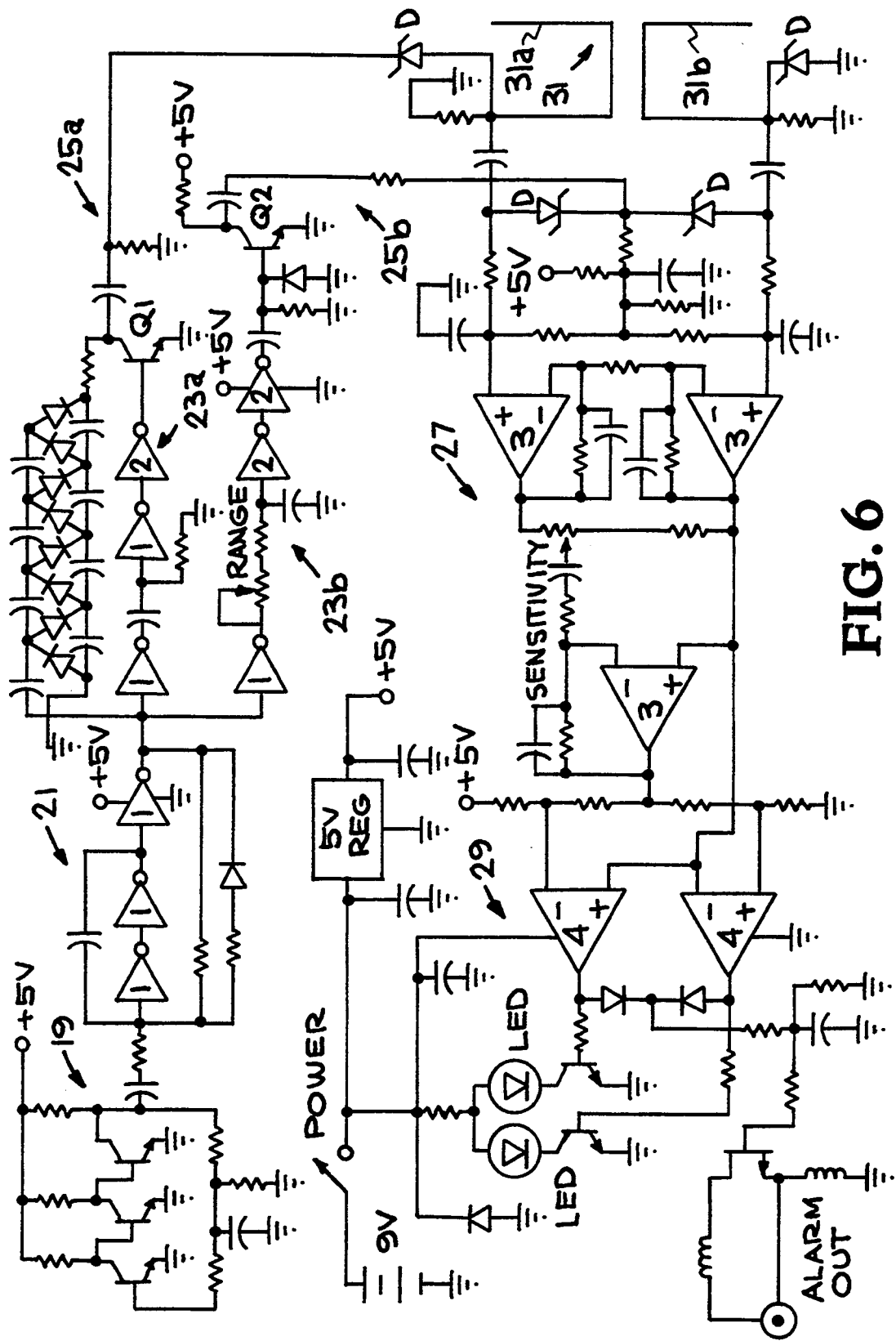
FIG. 6 is a schematic diagram of a VFIF medium range LTWB radar motion sensor.

Since many antennas exhibit increasing gain with increasing frequency, a step input applied to the transmit antenna will result in the radiation of the derivative of the step, i.e., an impulse. In the embodiments of FIGS. 5 and 6, a voltage step is applied to the transmit antenna. Both the transmit and receive antenna feedline may contain spectrum limiting or shaping filters for various purposes known to those skilled in the art.

The receive antenna 38 is connected to a UWB detector (receiver or sampler) 40, which is described in copending U.S. patent application Ser. No. 08/044,745, (IL-9091, RL-12,054, S-77,731) entitled "Ultra-Wideband Receiver" filed herewith, which is herein incorporated by reference. The UWB detector may also be a wideband sampling circuit, such as those incorporated by Tektronix, Inc. and Hewlett-Packard, Inc. in their standard sampling oscilloscopes. The sampler 40 is gated or strobed by the output of the adjustable delay 28 through impulse (or step) generator 42, thus causing the sampler 40 to sample a point in space corresponding to the two-way echo time to the target 44. Again, impulse/step generator 42 may be omitted if the adjustable delay pulse has sufficiently short risetime.

The output of the UWB detector 40 is averaged in an integrator 46 with a time constant that is substantially longer than the PRI of the radar, typically 10 ms in a motion sensor. At a PRI of 1 μs, 10,000 pulses are averaged. This average value represents the sum of the radar reflections and other radar clutter, such as direct antenna to antenna coupling.

The method can be implemented by averaging two or more pulses. However, preferably a large number, i.e. 1,000 to 10,000 pulses, will be averaged. The transmitted pulses typically have a pulse width of about 5 ns or less, and more preferably about 1 ns or less. The PRI typically is in the range of 100 ns to 100 μs.

If the radar reflectivity changes at the range being sampled, the average will change, and this change is sensed by the differentiator 48. The output of the differentiator 48 triggers a comparator circuit 50, which in turn can activate an alarm. Comparator 50 compares the output of differentiator 48 to a preset Vref. The sensitivity is controlled by Vref.

For simplicity, this invention uses an analog integrator and differentiator. A digital equivalent may be used at added complexity. In linear systems, the order of the integrator and differentiator may be interchanged. Further, the cascaded integration and differentiation process resembles a bandpass filter in the frequency domain, and so a bandpass filter 52 may be used for this combined function. Typical filter constants are: low frequency corner at 1 Hz and high frequency corner at 10 Hz, for motion sensing of people.

Figure 2:
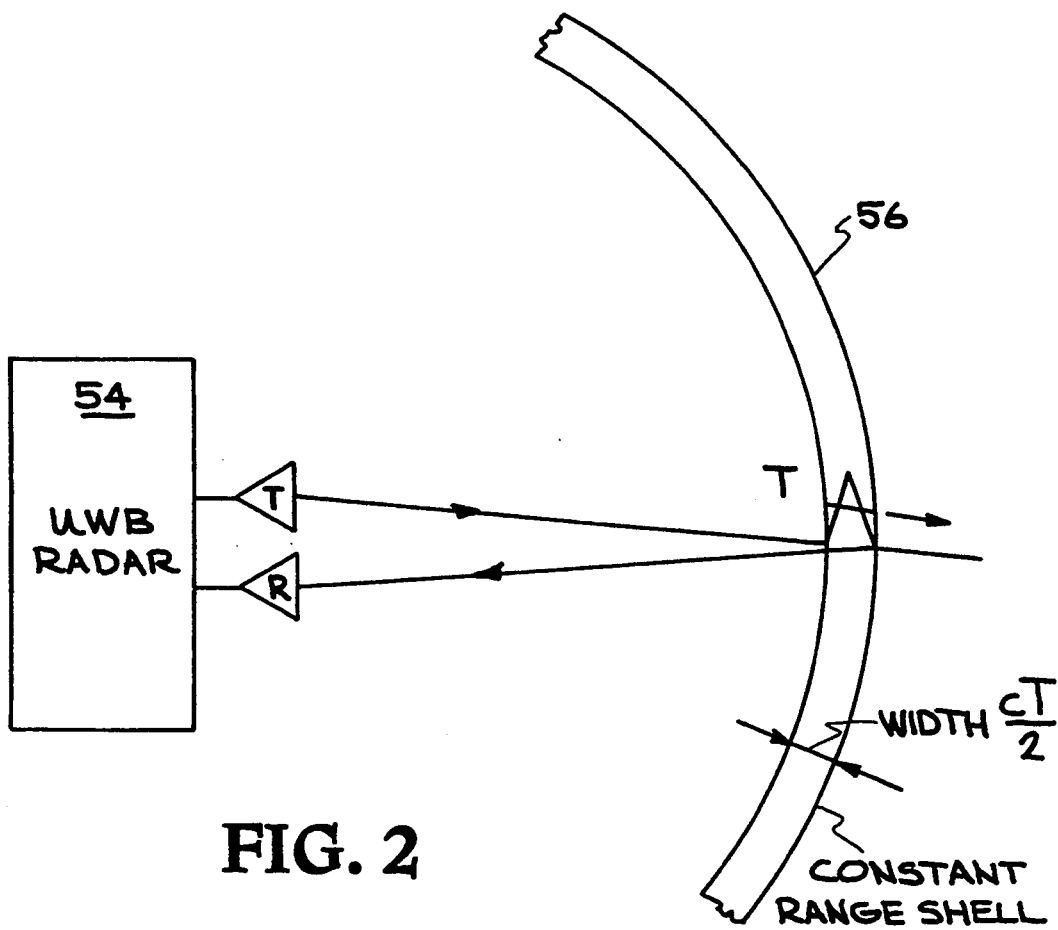
FIG. 2 illustrates a UWB radar constant range shell.
Figure 3A:
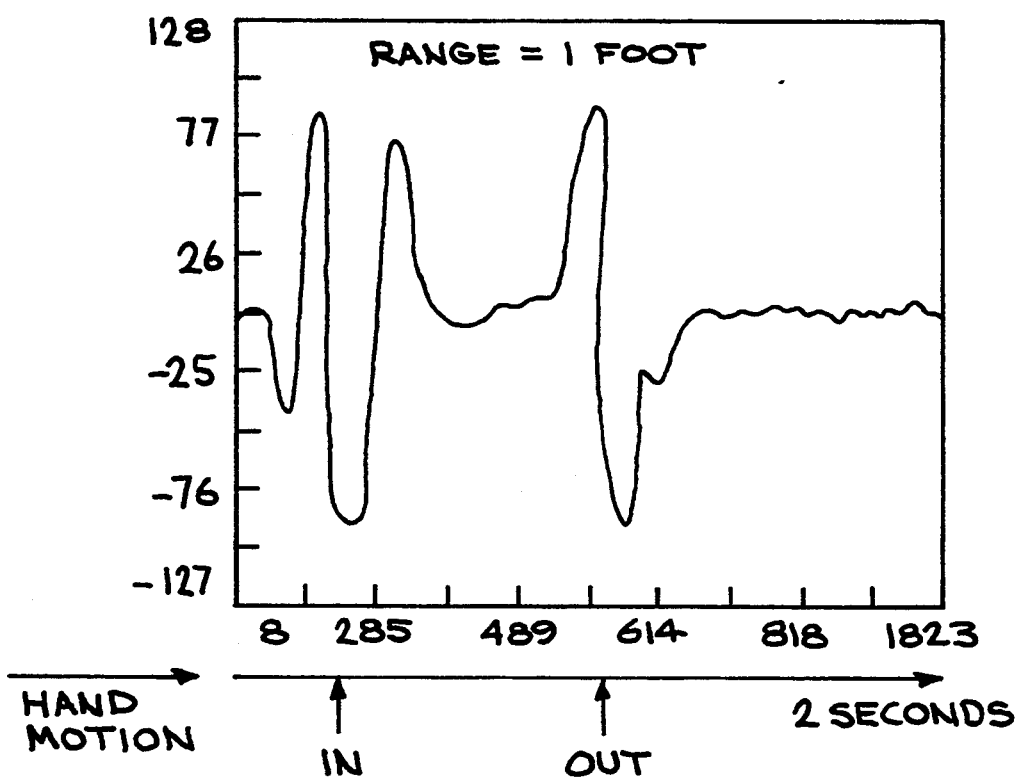
FIGS. 3a-d are various UWB radar motion detection signals.
Figure 3B:
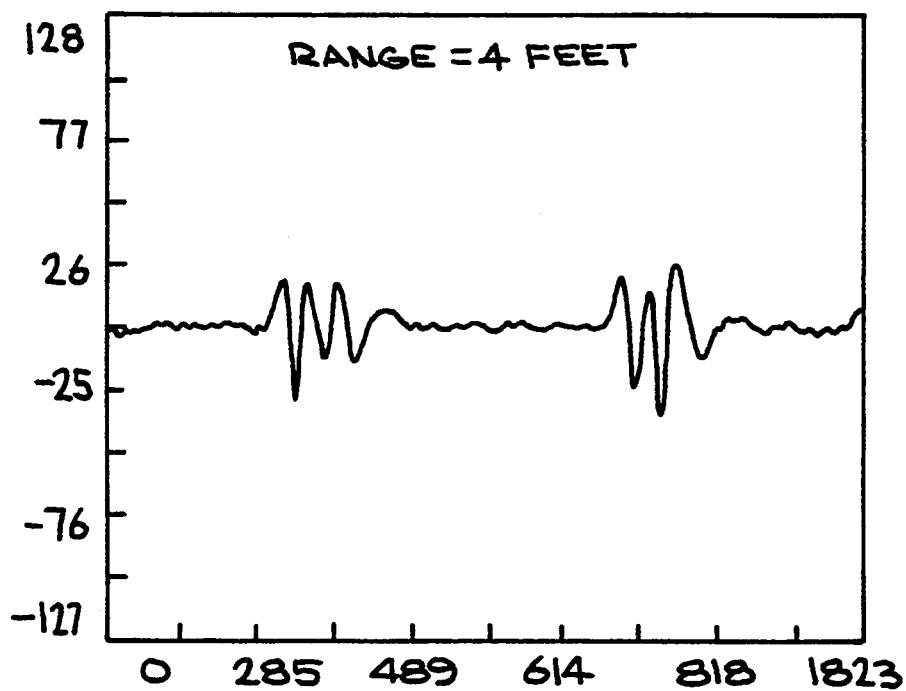
Figure 3C:
Figure 3D:
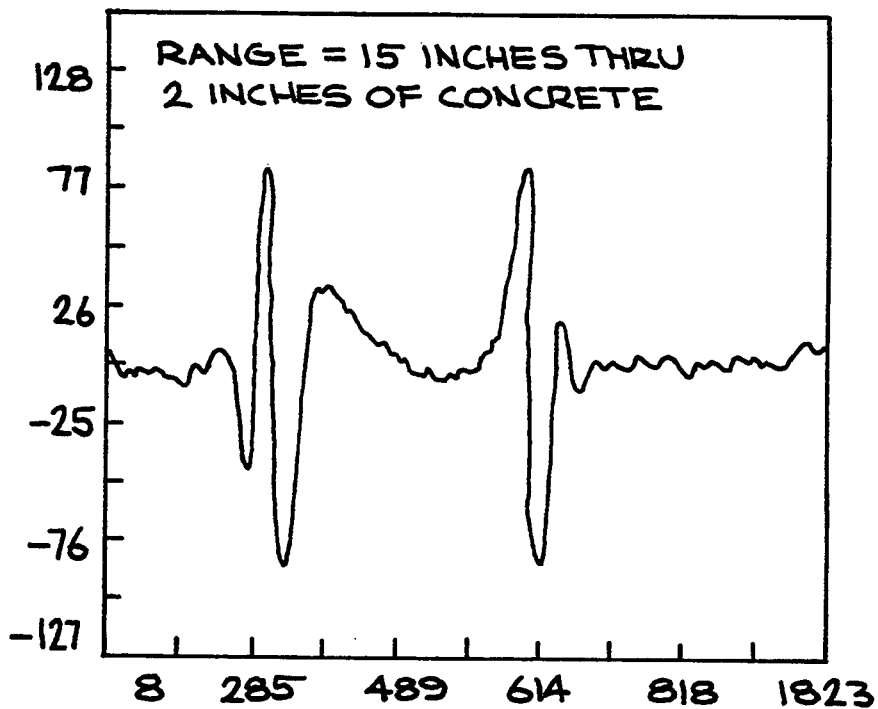

The UVVB pulse-echo system 54 typically operates at a constant sampling delay, or at a constant range, as depicted in FIG. 2. Due to the short impulse emitted, an effective spherical shell 56 is projected in space. The thickness of the shell is directly related to the sampling pulse width, which is generally set to be equal to the transmit pulse width T. The constant range shell then has a thickness of cT/2 where c is the pulse velocity.

FIGS. 3a-3d show data obtained from the UWB radar of FIG. 5. The horizontal scales are a slow time axis, corresponding to a 2 second time lapse. The vertical scale is the output from the UWB detector-integrator-differentiator. In FIGS. 3a-3d, a human hand is inserted into and then removed from the shell within the two second time scale, and the resulting signals are indicated for several ranges (1 ft. in FIG. 3a, 4 ft. in FIG. 3b, 15 in. in FIGS. 3c-d), and with several materials (6 in. of text books in FIG. 3c, 2 in. of concrete in FIG. 3d) between the radar and the target. Both insertion and removal of the hand are clearly shown.

Figure 4:
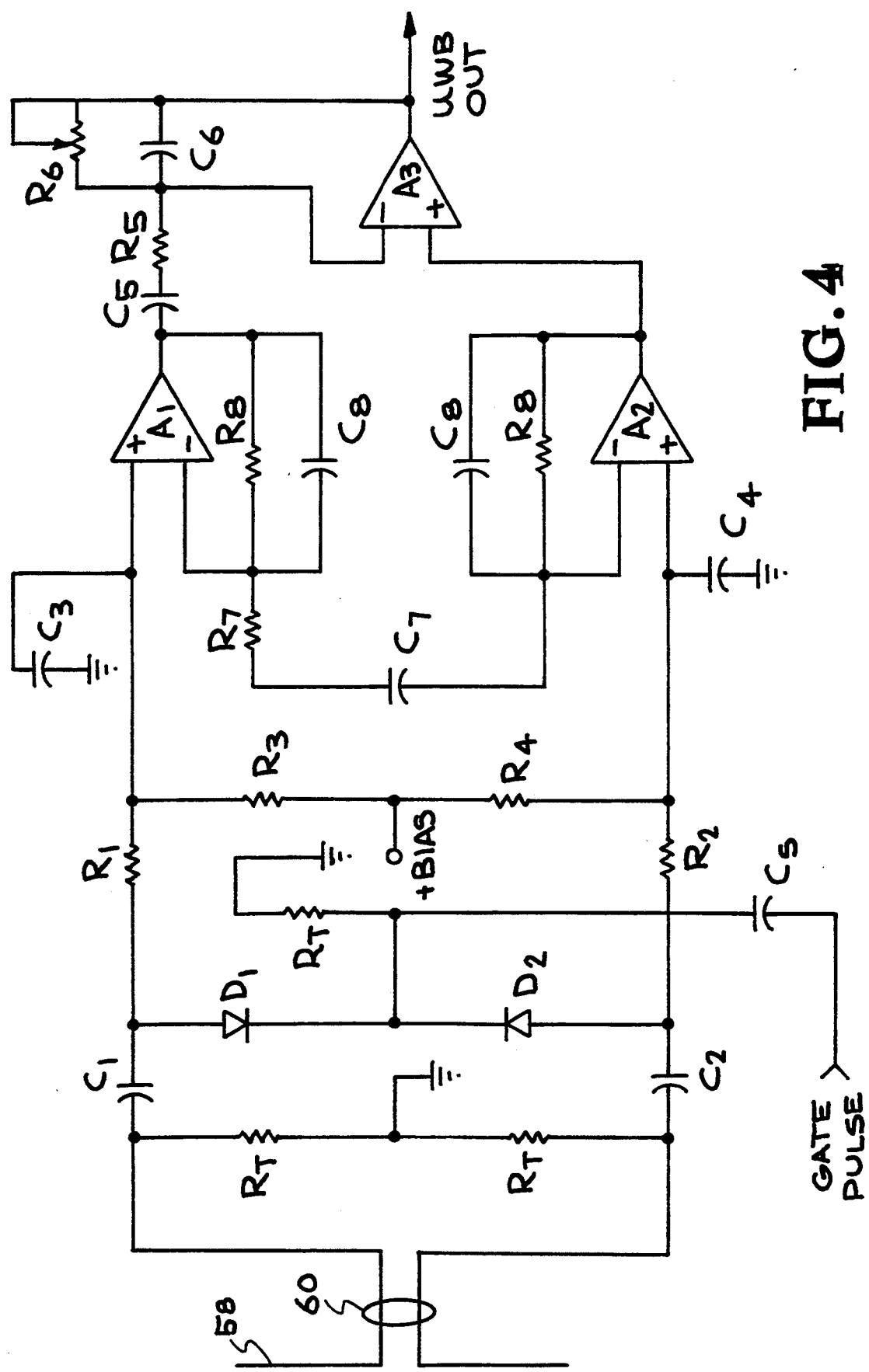
FIG. 4 is a schematic diagram of a UWB receiver in a UWB radar motion detector.

FIG. 4 shows a differential UWB receiver designed for use in UWB radar motion detector. A broadband dipole antenna 58 is connected to a twisted pair transmission line 60. Each wire of line pair 60 is connected through a capacitor C1 or C2 and series resistor R1 or R2 to the positive input of an operational amplifier A1 or A2. The junctions between C1-R1 and C2R2 are connected to a pair of diodes D1, D2 whose anodes are connected to the junctions and whose cathodes are connected together. A gating pulse is applied to the common cathode junction between D1-D2. The gating pulse line may include a capacitor $C_S$. The input line pair 60 and gating pulse input line are all terminated in resistors $R_T$. The positive inputs of A1, A2 are also connected through resistors R3, R4 respectively to a +Bias voltage. The positive inputs of A1, A2 are also connected through capacitors C3, C4 to ground. C3 and C4 can be omitted if there is sufficient input capacitance on A1, A2, or if RF rejection is not necessary or desired. The output of A1 is connected through C5 and R5 to the negative input of operational amplifier A3 and the Output of A2 is connected to the positive input of A3. The output of A3 is fed back to the negative input of A3 through capacitor C6 and parallel variable resistor R6. Resistor R6 is adjusted to control sensitivity. The negative inputs of A1, A2 are connected together through C7 and R7 and are connected to the output of A1, A2 through C8 and parallel R8.

In an illustrative embodiment C1=C2=22 pF, R1=R2=10K, $R_T$=68 ohm, D1 and D2 are M-Pulse MP2612 diodes, the gate pulse is −8 V with 200 ps edge and 1 μs PRI generated by Metellics step recovery diode MMD 805-828 input through a 0.5 pF capacitor, R3=R4=10m, +Bias=+5 V, C3=C4=0.01 μF, A1-A3 are TL074 op amps, C5=220 μF, R5=1K, C6=0.2 μF, R6=100K (variable), C7=4.7 μF, R7=47K, C8=3300 pF, R8=2.2M. If C3, C4 are omitted, then C1=C2=0.01 μF.

FIG. 5 is a schematic of a micropower UWB radar motion sensor. A series of CMOS logic gates (labeled I1) form the PRI generator (33 kHz oscillator) 21, which is connected through buffer gates (I2) to the delay circuits 23a,b and the impulse generators 25a,b. Noise generator 19 is connected to oscillator 21. The delay means 23a is just the wire (i.e. no delay), while the delay means 23b is formed of the resistors associated with switch S. The in, pulses are finally generated by step recovery diodes (SRD), supplied by Metellics Corp. of Sunnyvale, Calif. and specified to produce 100 ps transitions or faster. The transmit (T) and receiver (R) antennas are 6″ bow-tie shaped dipoles or 3″ wire monopoles. The UWB receiver 27 formed of op amps (I3) is of the type shown in FIG. 4 and contains the integrator and differentiator in the form of various capacitors associated with the circuit. The switch S in the gating pulse path and in the UWB receiver is used to select the range (6′ or 12′). An alarm circuit 29 is comprised of op amps I4, and includes a bipolar comparator and a driver circuit to sound an alarm after detection. The IC's are I1=CD4069, I2=74HC04, I3=TLC27L4, I4=TLC27L2. Not shown are a +3 V voltage regulator and +6 V penlight batteries. Because of the low duty cycle and small power consumption, the batteries last for several years in continuous operation.

FIG. 6 shows a VHF security alarm circuit, operating at a transmit pulse width of 2 ns. The waveform that is applied to the 18″ dipole antenna 31 is essentially a voltage step that is effectively differentiated, with ringing, by the antenna. The PRI generator (100 kHz oscillator) 21, and buffers in the transmit and receive (strobe) paths are formed by CMOS IC's I1 and I2, which are 74HC04 invertors. This IC costs less than $0.50 and generates stable, jitterfree delays from zero to 200 ns. Delay means 23a provides no delay, while delay means 23b is formed of potentiometer R. The impulse generators 25a,b include transistors Q1=2N5109 and Q2=2N2369. Noise generator 19 is connected to oscillator 21. The two halves 31a,b of a dipole antenna are connected to the inputs of UWB receiver 27 which drives alarm circuit 29. The IC's are I3=TLC27L4 and I4=TLC27L2 op amps. The Schottky diodes D are 1N5711. Range delay adjustment is provided by a simple potentiometer R in the strobe line. This circuit is similar to FIG. 5. It runs on batteries and its antennas are one meter in length rather than 6″.

The invention is thus based on RCS (radar cross section) averaging at a fixed range cell using averaging circuits, plus averaged RCS change detection. A fixed range is stared at, and a large number of return pulses are averaged. Changes in the average are then sensed as motion.

The invention also includes RCS averaging across a range sweep using averaging, plus averaged RCS change detection. Virtually all pulse-echo radars sweep the adjustable delay, or range delay, across a span while averaging a relatively small number of pulses, so individual "blips" may show up. In this invention, the averaging time constant can be set to be larger than the range scan time such that the entire sweep is averaged. Changes in this average represent motion somewhere within the range sweep.

Although individual "blips", or targets at particular ranges are diminished by the averaging process, noise levels are equally reduced by the averaging process, so the signal-to-noise ratio for changes in the blip remains the same. LTWB reflections off people are a highly variable function of aspect angle, so a person moving within the averaged range sweep will produce a detectable fluctuation. This sweep averaging technique is intended as a simplification to UWB motion sensor hardware.

Figure 7:
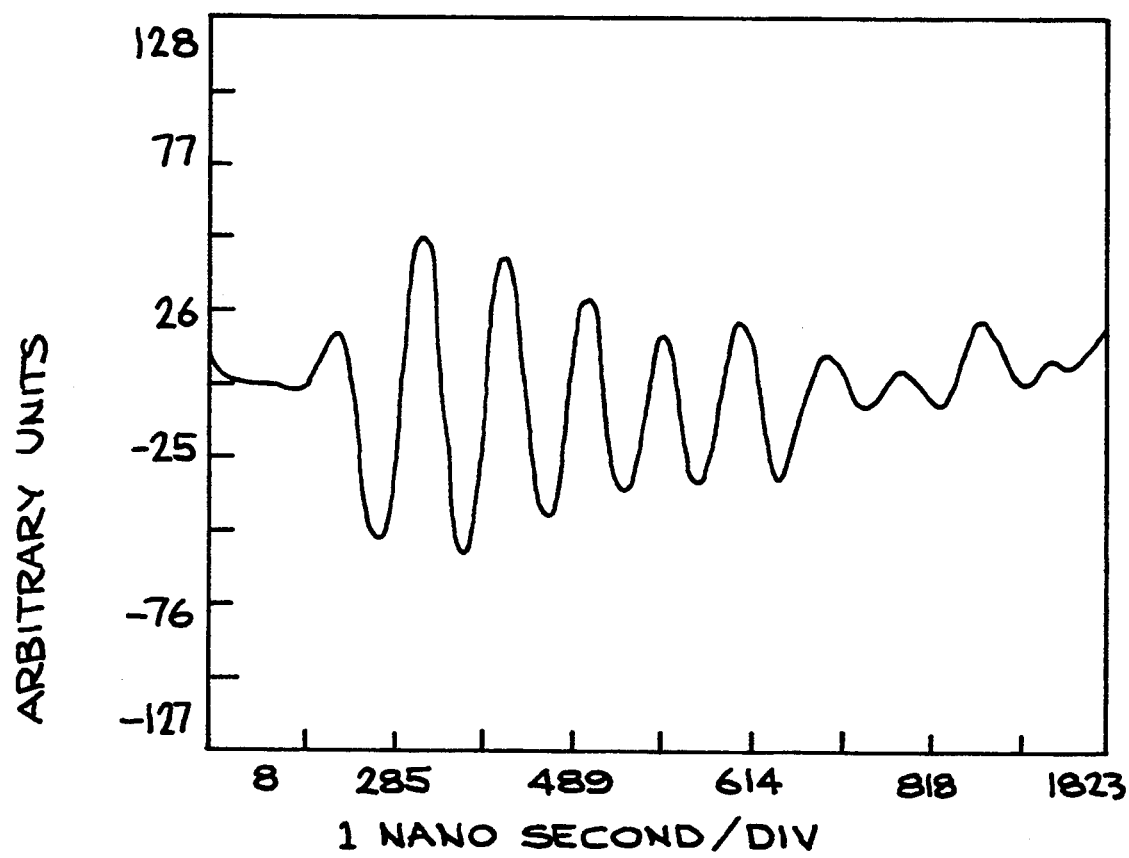
FIG. 7 shows dipole antenna pair ringdown.

The invention also includes an antenna ringdown method of motion detection across a range span, using averaging circuits, plus averaged RCS change detection. FIG. 7 shows typical antenna ringdown produced by a transmit/receive dipole pair when excited by a fast rising voltage step. UWB motion sensors operate primarily at a detection range corresponding to the time of flight of the leading edge of the transmitted pulse. Ringing that is trailing the leading edge appears later in tinge, while in space, ringing appears at a range closer to the radar, for a fixed sampling delay. Thus, for a given range delay setting, ringing pulses generate an outermost detection shell corresponding to the leading pulse, and successive inner detection shells located by the periodicity of the ringing.

The advantage to ringing is that it generates an effective range sweep since multiple ranges become active for motion sensing. Yet, range sweeping hardware is eliminated and the use of simple dipole antennas is allowed.

Another advantage to this technique, or to an averaged range sweep, is that if a target manages to evade the outer detection shell, the inner shells may still be activated. This situation occurs when the target echo from the outer range shell is too small to be detected. It also prevents a person from walking up to a UWB motion detector without setting it off.

As the antenna rings down, ringing amplitude decreases. Since successive ringing cycles appear at closer range, diminished amplitude helps maintain constant sensitivity.

Figure 8A:
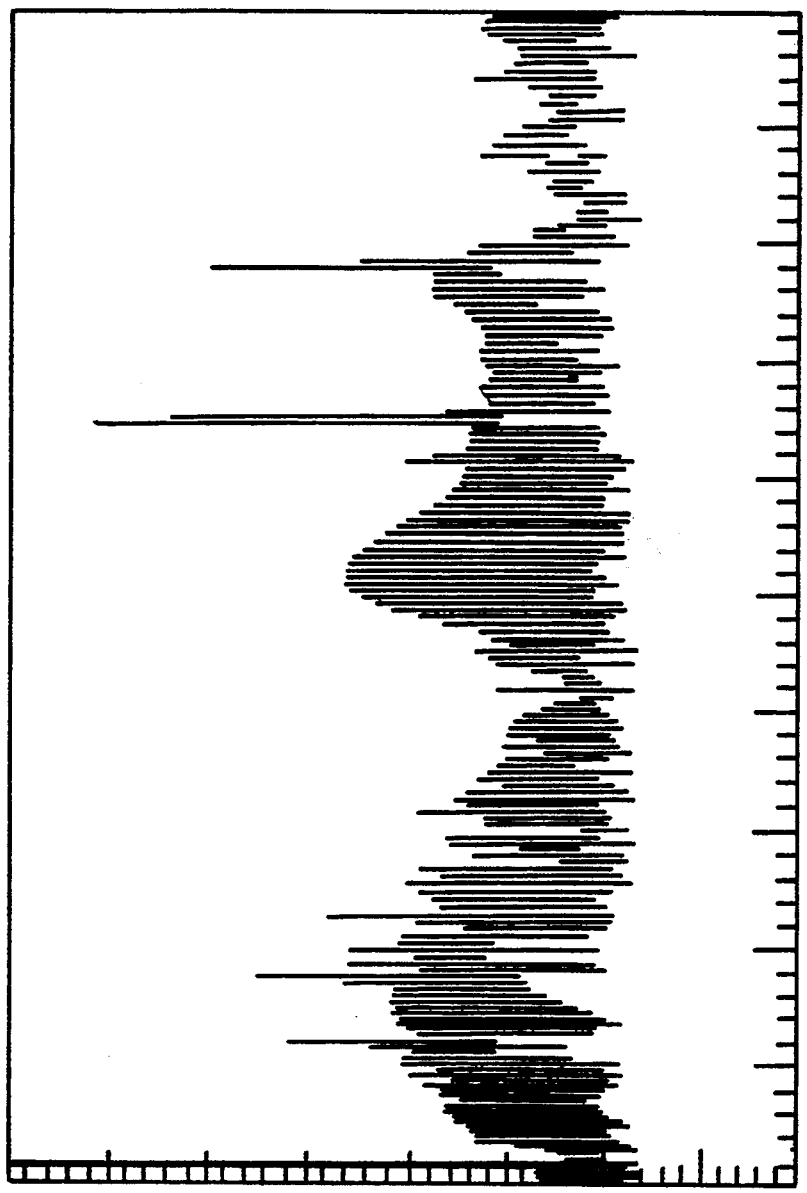
FIGS. 8a-b show UWB spectrum with non-dithered and dithered PRI operation.

The invention further includes randomly or pseudo-randomly dithered PRI operation. FIG. 8a shows the LTWB emission spectrum when the PRI is steady, or is not dithered. It consists of spectral lines located at harmonics of the pulse repetition frequency (PRF). The envelope formed by the spectral lines is identical in shape to the spectrum produced by a single impulse. (The tall spikes are local TV stations.)

Figure 8B:
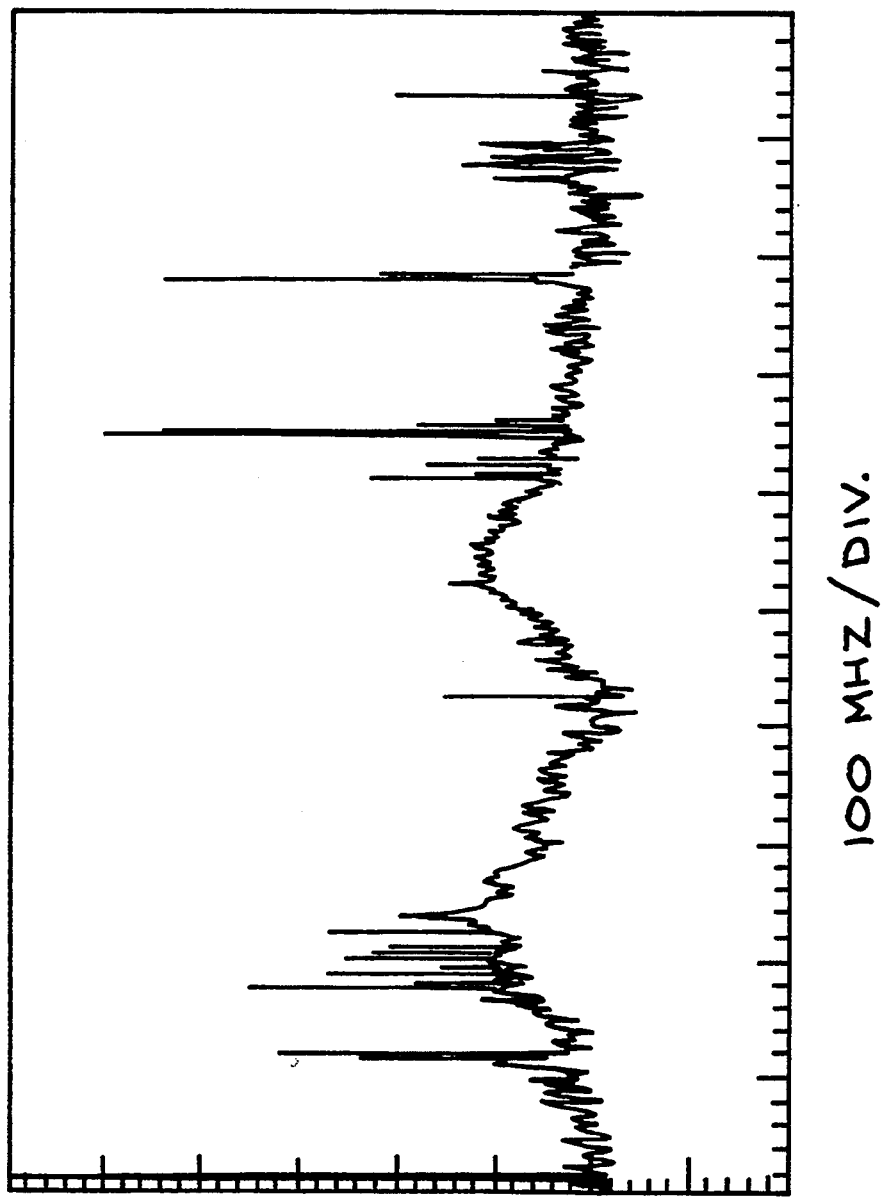

If either random noise or code-generated pseudo-random PRI modulation, or dither, is added, as shown in FIG. 8b, the emission spectrum can be spread to resemble the shape of a single impulse. Since the energy that was concentrated in individual lines is spread out, the peak amplitude of the spectrum is reduced. Interference to conventional receivers is reduced accordingly, and resembles thermal noise.

PRI dithering affects the pulse repetition interval only, and not the pulse-echo delay time. While most commercial sampling circuits do not tolerate PRI dither, the receiver circuits used in this invention have excellent independence from PRI variations.

A high level of pulse integration, e.g., 10,000 pulses, averages out interference in the receiver, and is thus a form of time domain tuning, since it accomplishes in the time domain what tuned circuits accomplish in the frequency domain. However, if an interfering signal has a frequency that is close to a multiple of the radar PRF, beat frequencies can form that appear in the averaged signal, (although this has not been observed in practice). By applying PRI dither, the same amount of averaging occurs, but there is no steady PRF with which to form beat frequencies. PRI dither is not per se unique, but is utilized here in UWB motion sensors.

According to the invention, the noise spectrum should lie above the UWB detection bandwidth. This reduces or eliminates any residual dither noise appearing at the UWB detector output, and eases the noise rejection requirements imposed on the UWB detector.

Figure 9:
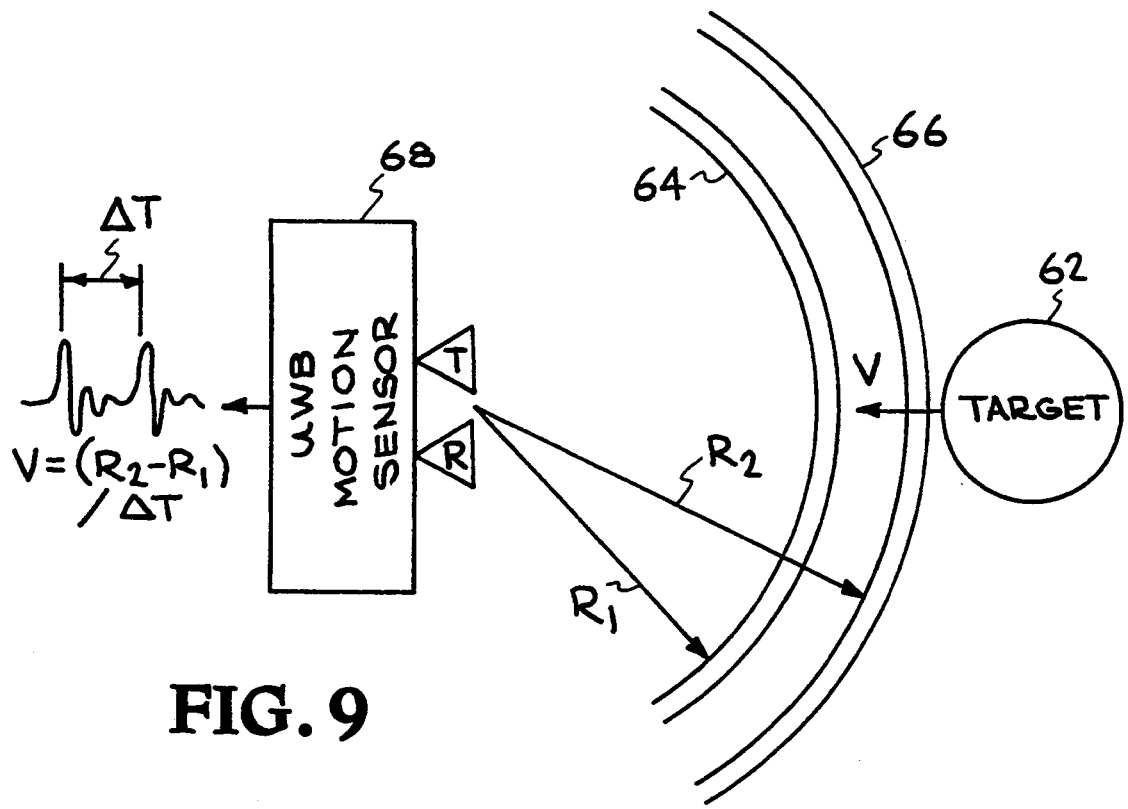
FIG. 9 illustrates dual shell velocity measurement.

The invention further provides absolute velocity measurement using dual range motion sensing. In automotive and other applications, motion sensing plus velocity measurement is desirable. FIG. 9 shows a dual detection shell scheme which is based on either of two methods described below to project two detection shells. As the target 62 traverses the shells 64 and 66 at R1 and R2, motion signals are generated which are detected by UWB motion sensor 68. The time difference between the detection events stemming from R1 and R2 can be used to determine radial velocity. The dual range principles can be extended to more than two shells or ranges.

Figure 10:
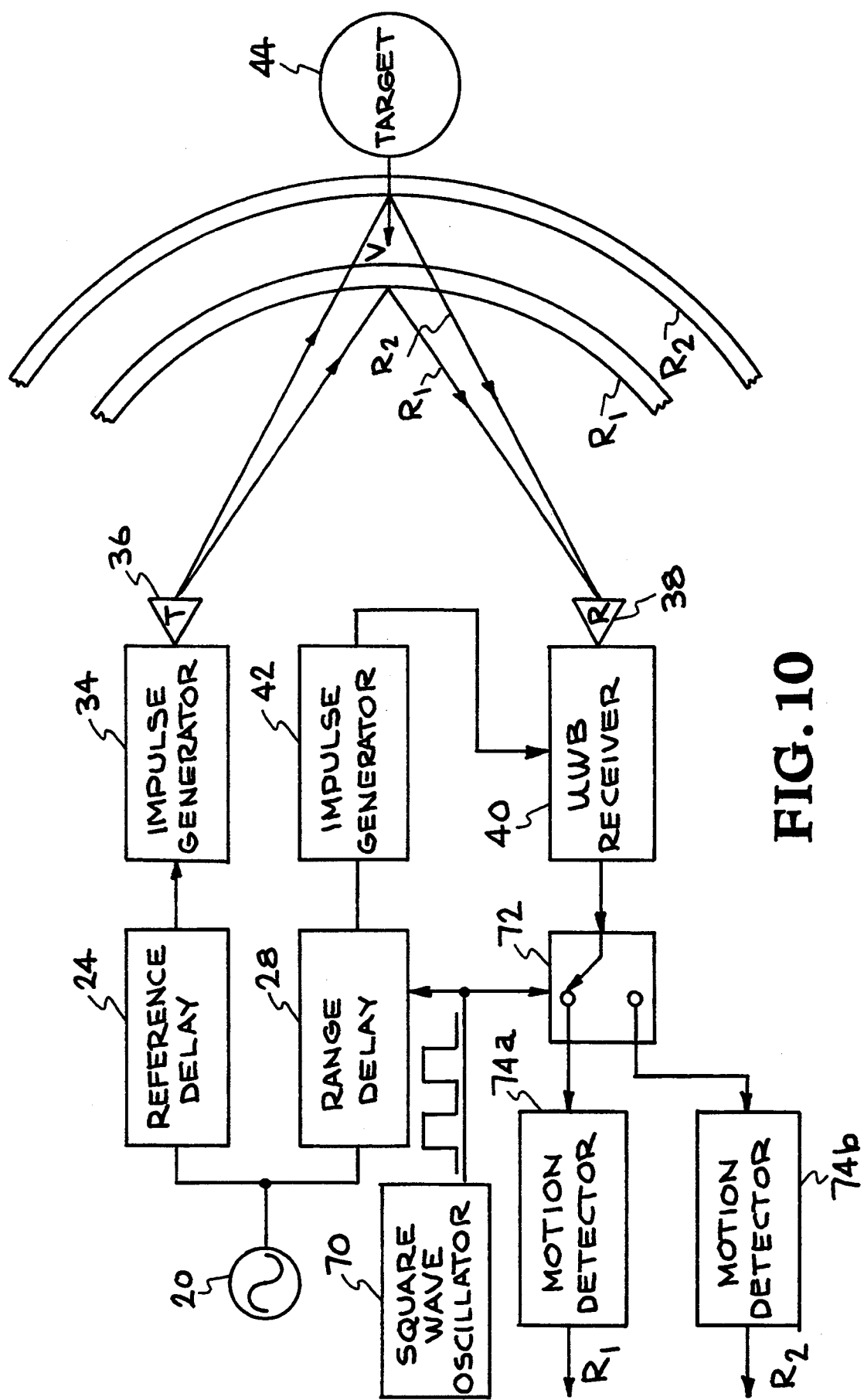
FIG. 10 is a schematic diagram of a time multiplexed dual range shell velocity measurement system.

One dual detection scheme is time multiplexed dual range operation. FIG. 10 depicts the scheme of FIG. 1 with a time multiplexed range circuit added. A squarewave oscillator 70 runs at a slower rate than the PRF, e.g., at 0.5 PRF, so the radar alternately ranges at R1 for a period and then R2 for a period. As the detection range is alternated, an analog switch 72 is toggled in synchronism, such that the two range signals from the UWB detector are routed to separate integrators and motion detection circuits 74a,b. The remaining components are the same as in FIG. 1.

The squarewave period is much shorter than the shortest traverse time associated with R1 and R2. In practice, R1 and R2 may differ by one foot, and for the fastest automotive environment, the R1–R2 traversal would be several milliseconds, much longer than the $\sim 1$ $\mu$s period of the squarewave oscillator.

Thus, with the addition of a small amount of circuitry, velocity can be measured. This feature does not require additional antennas. Unlike Doppler techniques, very low velocities can be measured.

Figure 11:
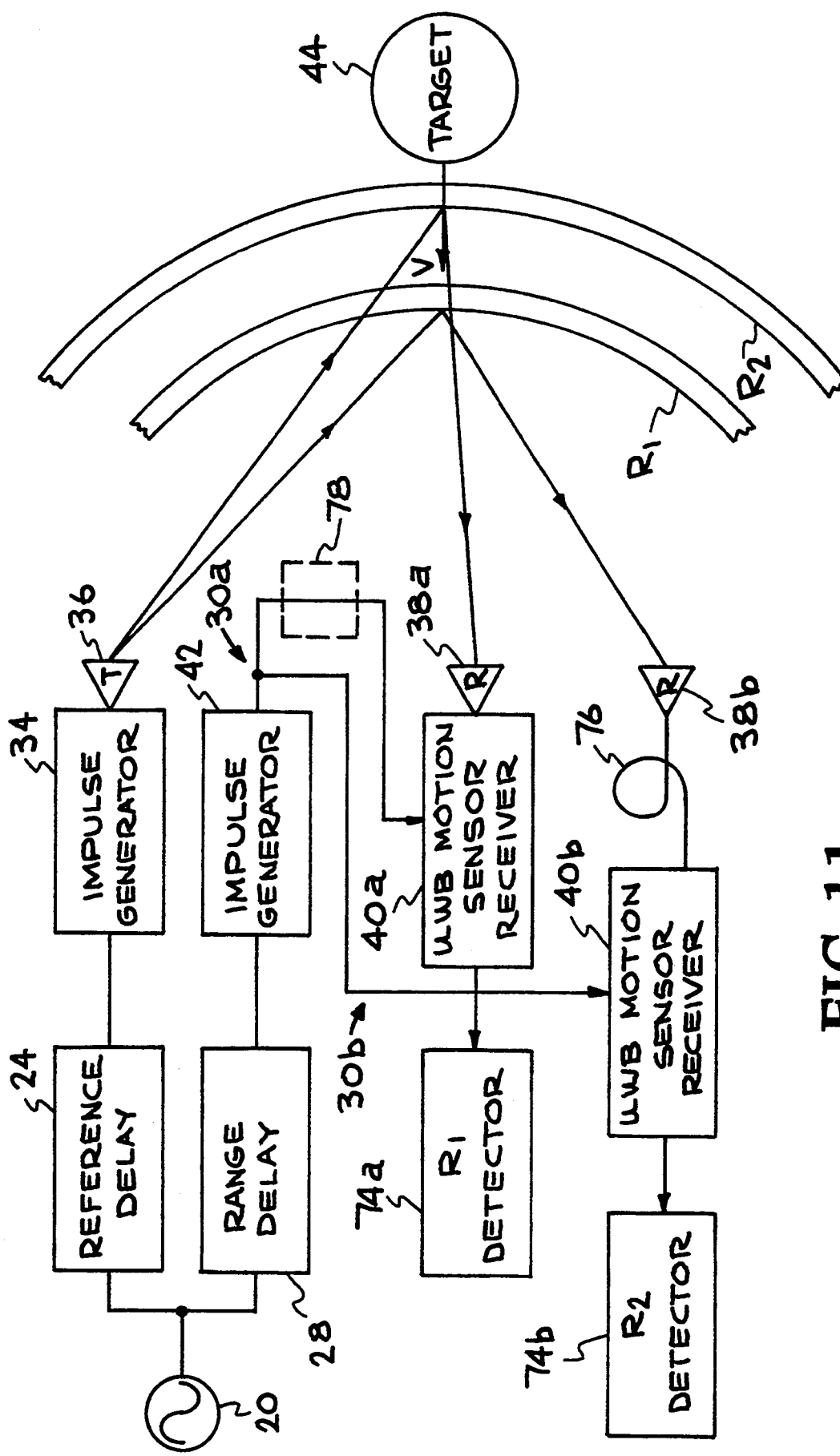
FIG. 11 is a schematic diagram of a dual delay velocity measurement system.

The other dual detection scheme is based on dual receive channels with a delay inserted into one channel. FIG. 11 depicts a dual shell velocity measurement scheme using the basic motion detector of FIG. 1 with an additional complete receiver channel 30b added. The second receiver 40b senses at a different range by having a cable delay 76 inserted in its antenna feedline. Alternately, a delay 78 can be inserted in the strobe line, e.g. in line 30a to receiver 40a. The remaining components are similar to FIGS. 1 and 10.

This system requires an additional antenna and a complete receiver, and thus is not preferred over the time multiplexed dual range system.

Unique features of UWB motion sensors are: excellent materials penetration; a sharply bounded, adjustable active range; low cost; multisensor operation; and potential for single chip implementation. This array of features will enable many new applications, the range of which is limited mainly by one's imagination. A few of the more prominent applications are the following:

Security Systems: UWB motion sensors may be placed behind walls, above ceilings, and below floors. One possible home installation would place UWB motion sensors above each room in the house and have their detection ranges set to six feet. At that range, the detection shell would reach down to a level that detects people, but would exclude detection of pets near the floor. In one test of the 100 ps motion sensor of FIG. 5, it was pointed through a wall into a hallway, and the range was set to span most of the width of the hallway. If a person hugged the far wall of the hallway, detection could be evaded, but an unknowing person would always be detected.

The area in front of a garage door can be protected by placing a UWB sensor inside the garage where it would be unseen by burglars, and where installation is simplified.

A single UWB VHF sensor may be placed in the center of a home and set to a detection range that projects an invisible detection shell around the entire house, providing complete home protection from a single, low-cost sensor. This concept has been successfully tested using the system of FIG. 6.

For police work, UWB sensors can be discretely placed outside rooms that are to be monitored for activity. Using the battery powered UWB VHF radar of FIG. 6, the sensitivity could be set so high that the slightest motion of a person in an adjacent room is detected. It does not appear possible for a living person to remain still enough to not set it off.

Novel Home Uses: UWB sensors can be built into junction boxes for use as concealed light switches and door openers. Homes of the future may have an invisible region near a wall where a hand can be waved to turn a light on. Doorways may be monitored by concealed UWB sensors to open them and turn lights on. UWB sensors may also help the handicapped.

Intelligent Appliances: With their unique ability to operate through plastic panels and to operate at close range, UWB sensors will find use in intelligent appliances that sense the presence of a person, or a person's hand, and respond accordingly. Lights can be turned on, doors can be opened, machines can be turned off for safety or convenience, ovens can be deactivated, etc.

Life Detector For Disaster Work: Buried earthquake and avalanche victims may be located with highly sensitive LTWB detectors. The superior penetration capability of UWB radar, as well as excellent close-range operation and high sensitivity will enhance prior work using FM-CW radar. The UWB VHF radar of FIG. 6 has detected respiration and possibly heartbeats at a 10 foot range.

Medical Applications: The 100 ps UWB radar of FIG. 5 has detected heart beats and arterial pulses at near-zero range (surface contact). Although most of the detected signal may be due to skin motion, there appears to be a deeper component. The medical significance is not known at this time. UWB radiation levels are well below the OSHA limit for continuous exposure to microwaves.

Automotive Collision Sensor: Most of the radar community has focused on millimeter-wave (MMW) radars for automotive use. Current cost projections for these radars are $500 or more. Some of these radars are very microphonic, since the MMW-radar wavelengths and mechanical vibrations are of similar dimensions. Further, MMW radars will require windshield wipers due to their inability to penetrate water, mud and snow cover. MMW radar proponents overlook the fundamental fact that radar works best when the radar wavelength is on the same order as the target dimensions.

Thus, one or two meter wavelength VHF radar would be most appropriate for sensing automobiles.

UWB VHF radar antennas may consist of elementary wire dipoles embedded in plastic body sections or embedded in windows. Although the overall dipole length should be on the order of 0.5–1.0 meters, considerably shorter dipoles will also work since the limited detection range and large radar cross section of cars permits operation with high system losses.

Detection ranges from 1 to 10 feet are practical with omnidirectional antennas. Using antennas embedded in the tail light and parking light lenses, detection shells can be projected to cover the rear, sides and front of the vehicle. These antennas may be connected to a central UWB module using low cost coaxial cables. The cost of the UWB module could be on the order of $10. Triangulation might eventually be used to achieve sharply-controlled synthetic beamwidths.

UWB motion sensing offers three levels of alarm discrimination: radar cross-section, or object size; precise detection range; and velocity measurement. All of these discriminants may easily be scaled to match vehicle speed.

Changes and modifications in the specifically described embodiments can be carried out without departing from the scope of the invention which is intended to be limited only by the scope of the claims.

I claim:

1. An ultra-wideband (UWB) radar motion sensor, comprising:
   a pulse repetition interval generator;
   a fixed reference delay means connected to the pulse repetition interval generator;
   a transmit pulse generator connected to the reference delay means;
   a transmit antenna connected to the transmit pulse generator;
   an adjustable delay means connected to the pulse repetition interval generator;
   a gating pulse generator connected to the adjustable delay means;
   an UWB radar receiver connected to the gating pulse generator;
   a receiver antenna connected to the UWB receiver;
   signal processing means connected to the UWB receiver.

2. The sensor of claim 1 further comprising alarm means connected to the signal processing means.

3. The sensor of claim 1 further comprising a noise generator connected to the pulse repetition interval generator.

4. The sensor of claim 1 further comprising range adjustment means connected to the adjustable delay means.

5. The sensor of claim 1 wherein the signal processing means comprises an integrator followed by a differentiator.

6. The sensor of claim 1 wherein the signal processing means is a bandpass filter.

7. The sensor of claim 1 wherein the pulse repetition interval generator is a dithered pulse generator.

8. The sensor of claim 1 further comprising a square wave oscillator connected to the adjustable delay means for repetitively switching between two fixed ranges and an analog switch connected to the output of the UWB receiver and to the square wave oscillator for switching the UWB receiver output to separate motion detectors for each range.

9. The sensor of claim 1 further comprising a second UWB radar receiver connected to the gating impulse generators, a second receiver antenna connected to the second UWB receiver, and a delay line positioned either between the second receiver antenna and second UWB receiver, or inbetween the gating impulse generator and one of the UWB receivers.

10. The sensor of claim 1 wherein the UWB radar receiver averages about 1,000 to 10,000 pulses.

11. The sensor of claim 1 wherein the transmit and receiver antennas are formed of a dipole pair which exhibits antenna ringdown.

12. The sensor of claim 1 wherein the transmit pulse generator comprises a logic gate connected to a step recovery diode.

13. The sensor of claim 1 wherein the transmit pulse generator comprises a logic gate connected to a high speed bipolar transistor.

14. The sensor of claim 1 wherein the adjustable delay means comprises a resistor-capacitor (RC) network between a first logic gate and a second logic gate.

15. The sensor of claim 1 wherein the pulse repetition interval generator comprises a CMOS oscillator.

16. The sensor of claim 1 wherein the pulse repetition interval generator comprises a resistor-capacitor (RC) oscillator with a nonlinear resistance network.

17. The sensor of claim 7 wherein the dithered pulse generator comprises a bipolar transistor, a base resistor, and an amplifier.

18. The sensor of claim 2 wherein the alarm means triggers on an increase or decrease in average detected signal.

19. The sensor of claim 1 wherein at least one of the transmit pulse generator and the gating pulse generator comprises means to limit the pulse width or duty cycle.

20. The sensor of claim 1 wherein the transmit antenna comprises a single dipole with the transmit pulse applied to one terminal of the dipole and the receiver connected to one or both terminals of the dipole.

* * * * *

US005361070B1

REEXAMINATION CERTIFICATE (4084th)

United States Patent [19]
McEwan

[11] B1 5,361,070
[45] Certificate Issued May 16, 2000

[54] ULTRA-WIDEBAND RADAR MOTION SENSOR

[75] Inventor: Thomas E. McEwan, Livermore, Calif.

[73] Assignee: The Regents of the University of California, Oakland, Calif.

Reexamination Requests:
No. 90/004,875, Dec. 19, 1997
No. 90/004,971, Apr. 20, 1998
No. 90/005,248, Feb. 5, 1999

Reexamination Certificate for:
Patent No.: 5,361,070
Issued: Nov. 1, 1994
Appl. No.: 08/044,717
Filed: Apr. 12, 1993

[51] Int. Cl.[7] .................................................. G01S 13/00
[52] U.S. Cl. .............................................................. 342/21
[58] Field of Search ........................................ 342/21, 28

[56] References Cited

U.S. PATENT DOCUMENTS

| | | |
|---|---|---|
| 2,671,896 | 3/1954 | De Rosa . |
| 3,096,491 | 7/1963 | Ball et al. .................................... 331/87 |
| 3,175,214 | 3/1965 | Ramsay et al. . |
| 3,195,130 | 7/1965 | Adrian . |
| 3,402,370 | 9/1968 | Ross .......................................... 333/20 |
| 3,418,604 | 12/1968 | Ross .......................................... 333/20 |
| 3,423,754 | 1/1969 | Gunn . |
| 3,495,190 | 2/1970 | Ross .......................................... 333/28 |
| 3,569,877 | 3/1971 | Robbins ....................................... 335/5 |
| 3,587,107 | 6/1971 | Ross .......................................... 343/739 |
| 3,612,899 | 10/1971 | Ross .......................................... 307/106 |
| 3,631,351 | 12/1971 | Paine et al. . |
| 3,634,755 | 1/1972 | Nicolson ............................... 324/57 R |
| 3,646,478 | 2/1972 | Ross ........................................... 307/106 |
| 3,659,203 | 4/1972 | Ross et al. .............................. 325/105 |
| 3,662,316 | 5/1972 | Robbins ............................ 340/167 R |
| 3,668,639 | 6/1972 | Harmuth ............................. 340/166 R |
| 3,678,204 | 7/1972 | Harmuth ............................. 179/15 BC |
| 3,680,100 | 7/1972 | Woerrlein . |

(List continued on next page.)

FOREIGN PATENT DOCUMENTS

WO 90/13048 11/1990 WIPO .
9113370 9/1991 WIPO .

OTHER PUBLICATIONS

IEEE 1992 International Microwave Symposium Digest, vol. III, Jun. 1, 1992, Albuquerque, New Mexico, pp. 1491–1494, XP 000344454 Toevs et al., "UWB Radar for Ground Vehicle Self Protect".

Harmuth, H., "Nonsinusoidal Waves for Radar and Radio Communication", Academic Press, New York (1981), pp. 119–143, 288, 293, 297, 302, 305.

Harmuth, H., "Antennas and Waveguides for Nonsinusoidal Waves", Academic Press, New York (1984), pp. 141–147.

Cook, J., "Proposed Monocycle–Pulse Very–High–Frequency Radar for Air–Borne Ice and Snow Measurement", *Trans. of the American Institute of Electrical Engineers*, vol. 79, Nov. 1960, pp. 588–594.

Instruction Manual, Type S–2 Sampling Head, copyright 1968, Tektronix, Inc., Beaverton, OR, pp. 3–1 to 3–3, 6–1, 6–2.

Harmuth, H., "A Generalized Concept of Frequency and Some Applications", *IEEE Transactions on Information Theory*, vol. IT–14, No. 3, May 1968, pp. 375–382.

Harmuth, H., "Application of Walsh Functions in Communications", IEEE Spectrum, Nov. 1969, pp. 82–91.

(List continued on next page.)

*Primary Examiner*—Mark Hellner

[57] ABSTRACT

A motion sensor is based on ultra-wideband (UWB) radar. UWB radar range is determined by a pulse-echo interval. For motion detection, the sensors operate by staring at a fixed range and then sensing any change in the averaged radar reflectivity at that range. A sampling gate is opened at a fixed delay after the emission of a transmit pulse. The resultant sampling gate output is averaged over repeated pulses. Changes in the averaged sampling gate output represent changes in the radar reflectivity at a particular range, and thus motion.

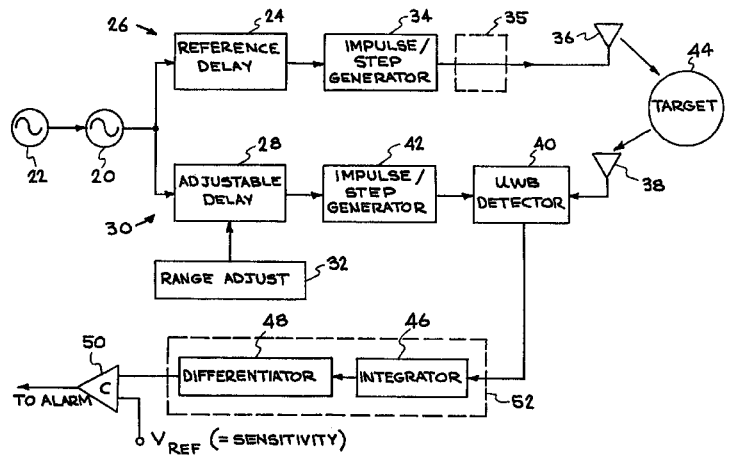

U.S. PATENT DOCUMENTS

| | | | |
|---|---|---|---|
| 3,693,080 | 9/1972 | Ross et al. | 324/58.5 A |
| 3,696,359 | 10/1972 | Ross et al. | 340/224 |
| 3,705,981 | 12/1972 | Harmuth | 235/193 |
| 3,714,655 | 1/1973 | Ross et al. | 343/100 R |
| 3,721,912 | 3/1973 | Ross | 328/151 |
| 3,728,632 | 4/1973 | Ross | 325/38 R |
| 3,735,398 | 5/1973 | Ross | 343/7 ED |
| 3,739,392 | 6/1973 | Ross et al. | 343/840 |
| 3,750,025 | 7/1973 | Ross | 325/321 |
| 3,750,125 | 7/1973 | Ross et al. | 340/258 C |
| 3,757,290 | 9/1973 | Ross et al. | 340/23 |
| 3,763,318 | 10/1973 | Ross et al. | 179/15 A |
| 3,772,697 | 11/1973 | Ross | 343/13 R |
| 3,786,413 | 1/1974 | Ross et al. | 340/58 |
| 3,789,413 | 1/1974 | Ross et al. | 343/113 R |
| 3,794,996 | 2/1974 | Robbins et al. | 343/7 A |
| 3,801,976 | 4/1974 | Ross et al. | 340/258 R |
| 3,805,497 | 4/1974 | Ross | 56/10.4 |
| 3,806,795 | 4/1974 | Morey . | |
| 3,832,900 | 9/1974 | Ross | 73/290 R |
| 3,839,700 | 10/1974 | DeLorenzo et al. | 340/38 L |
| 3,858,204 | 12/1974 | Robbins et al. | 343/7 ED |
| 3,858,205 | 12/1974 | Ross | 343/7 ED |
| 3,866,152 | 2/1975 | Ross | 333/20 |
| 3,878,749 | 4/1975 | Woron | 84/1.01 |
| 3,934,252 | 1/1976 | Ross et al. | 343/7 VM |
| 3,971,990 | 7/1976 | Ross | 325/400 |
| 3,979,749 | 9/1976 | Ross et al. | 343/13 R |
| 3,995,212 | 11/1976 | Ross | 324/58.5 B |
| 4,008,469 | 2/1977 | Chapman | 343/5 NA |
| 4,017,854 | 4/1977 | Ross | 343/16 R |
| 4,072,942 | 2/1978 | Alongi | 343/5 |
| 4,099,118 | 7/1978 | Franklin et al. | 324/61 |
| 4,107,987 | 8/1978 | Robbins et al. | 73/151 |
| 4,150,375 | 4/1979 | Ross et al. | 343/7 VM |
| 4,152,701 | 5/1979 | Mara et al. | 343/8 |
| 4,188,595 | 2/1980 | Cronson et al. | 333/113 |
| 4,214,248 | 7/1980 | Cronson et al. | 343/756 |
| 4,241,346 | 12/1980 | Watson . | |
| 4,254,418 | 3/1981 | Cronson et al. | 343/112 CA |
| 4,291,289 | 9/1981 | Rao et al. | 333/240 |
| 4,344,705 | 8/1982 | Kompa et al. | 356/5 |
| 4,394,640 | 7/1983 | Ross | 340/23 |
| 4,414,549 | 11/1983 | Wichmann | 343/18 E |
| 4,430,653 | 2/1984 | Coon et al. | 343/5 NA |
| 4,443,799 | 4/1984 | Rubin . | |
| 4,497,252 | 2/1985 | Taylor | 102/214 |
| 4,506,267 | 3/1985 | Harmuth | 343/744 |
| 4,510,496 | 4/1985 | Ross | 343/5 BD |
| 4,596,023 | 6/1986 | Driver et al. . | |
| 4,641,317 | 2/1987 | Fullerton | 375/1 |
| 4,651,152 | 3/1987 | Harmuth | 342/13 |
| 4,688,041 | 8/1987 | Cronson et al. | 342/17 |
| 4,695,752 | 9/1987 | Ross et al. | 307/518 |
| 4,698,633 | 10/1987 | Lamensdorf et al. | 342/42 |
| 4,743,906 | 5/1988 | Fullerton . | |
| 4,743,908 | 5/1988 | Brassfield et al. | 342/113 |
| 4,751,515 | 6/1988 | Corum | 343/742 |
| 4,813,057 | 3/1989 | Fullerton | 375/37 |
| 4,862,174 | 8/1989 | Naito et al. | 342/1 |
| 4,905,008 | 2/1990 | Kawano et al. | 342/22 |
| 4,907,001 | 3/1990 | Harmuth | 342/159 |
| 4,975,703 | 12/1990 | Delisle et al. . | |
| 4,979,186 | 12/1990 | Fullerton . | |
| 5,020,374 | 6/1991 | Petroff et al. . | |
| 5,057,846 | 10/1991 | Harmuth | 342/204 |
| 5,084,706 | 1/1992 | Ross et al. . | |
| 5,095,312 | 3/1992 | Jehle et al. | 342/21 |
| 5,134,408 | 7/1992 | Harmuth | 342/21 |
| 5,146,616 | 9/1992 | Tang et al. | 455/103 |
| 5,148,174 | 9/1992 | Harmuth | 342/21 |
| 5,148,175 | 9/1992 | Woolfolk | 342/95 |
| 5,153,595 | 10/1992 | Harmuth | 342/22 |
| 5,159,343 | 10/1992 | Harmuth | 342/22 |
| 5,177,486 | 1/1993 | Kim et al. | 342/21 |
| 5,216,429 | 6/1993 | Nakagawa et al. | 342/450 |
| 5,216,695 | 6/1993 | Ross et al. | 375/59 |
| 5,223,838 | 6/1993 | Tang et al. | 342/13 |
| 5,226,328 | 7/1993 | Petroff et al. . | |
| 5,227,621 | 7/1993 | Kim et al. | 250/214.1 |
| 5,239,309 | 8/1993 | Tang et al. | 342/13 |
| 5,248,975 | 9/1993 | Schutz | 342/21 |
| 5,274,271 | 12/1993 | McEwan | 307/108 |
| 5,303,108 | 4/1994 | Higashionji et al. | 360/137 |
| 5,307,079 | 4/1994 | Ross | 343/822 |
| 5,307,081 | 4/1994 | Harmuth | 343/842 |
| 5,317,303 | 5/1994 | Ross et al. | 340/539 |
| 5,323,169 | 6/1994 | Koslover | 343/786 |
| 5,332,938 | 7/1994 | McEwan | 307/572 |
| 5,333,508 | 8/1994 | Petroff et al. . | |
| 5,337,054 | 8/1994 | Ross et al. | 342/93 |
| 5,345,471 | 9/1994 | McEwan . | |
| 5,353,303 | 10/1994 | Walthall . | |
| 5,363,108 | 11/1994 | Fullerton . | |
| 5,365,240 | 11/1994 | Harmuth | 343/701 |
| 5,389,939 | 2/1995 | Tang et al. | 343/754 |
| 5,420,589 | 5/1995 | Wells et al. . | |
| 5,455,593 | 10/1995 | Ross . | |
| 5,463,656 | 10/1995 | Polivka et al. . | |
| 5,471,162 | 11/1995 | McEwan | 327/92 |
| 5,486,833 | 1/1996 | Barrett | 342/204 |
| 5,523,758 | 6/1996 | Harmuth | 342/22 |
| 5,572,190 | 11/1996 | Ross et al. | 340/541 |
| 5,573,012 | 11/1996 | McEwan . | |
| 5,586,145 | 12/1996 | Morgan et al. . | |
| 5,610,907 | 3/1997 | Barrett . | |
| 5,627,995 | 5/1997 | Miller et al. . | |
| 5,640,138 | 6/1997 | Hinkley et al. | 340/323 R |
| 5,667,927 | 9/1997 | Kubota et al. | 430/109 |
| 5,677,927 | 10/1997 | Fullerton et al. | 375/200 |
| 5,687,169 | 11/1997 | Fullerton . | |
| 5,812,081 | 9/1998 | Fullerton | 342/221 |

OTHER PUBLICATIONS

Harmuth, H., "Historical Background and Motivation for the Use of Nonsinusoidal Functions", Transmission of Information by Orthogonal Functions, Second Edition, Springer Verlag (1972), pp. 1–9.

Harmuth, H., "Signal Selection and Synchronization", Transmission of Information by Orthogonal Functions, Second Edition, Springer Verlag (1972), pp. 282–291.

Harmuth, H., "Interference Caused by Additional Radio Channels Using Nonsinusoidal Carriers", Second Symposium and Technical Exhibition on Electromagnetic Compatibility, Montreaux, Jun. 1977, pp. 25–30.

Harmuth, H., "Selective Reception of Periodic Electromagnetic Waves with General Time Variation", IEEE Transactions on Electromagnetic Compatibility, vol. EMC–19, No. 3, Aug. 1977, pp. 137–144.

Harmuth, H., "Frequency–Sharing and Spread–Spectrum Transmission with Large Relative Bandwidth", IEEE Transactions on Electromagnetic Compatibility, vol. EMC–20, No. 1, Feb. 1978, pp. 232–239.

Davis, J. et al., "Some Physical Constraints on the Use of "Carrier–Free" Waveforms in Radio–Wave Transmission Systems", Proc. of the IEEE, vol. 67, No. 6, Jun. 1979, pp. 884–891.

Harmuth, H. et al., "Antennas for Nonsinusoidal Waves: I. Radiators", IEEE Transactions on Electromagnetic Compatibility, vol. EMC–25, No. 1, Feb. 19983, pp. 13–24.

Morente, J. et al., "Comment on 'Antennas for Nonsinusoidal Waves: I. Radiators'", IEEE Transactions on Electromagnetic Compatibility, vol. EMC–26, No. 1, Feb. 1984, p. 50.

Harmuth, H. et al., "Antennas for Nonsinusoidal Waves: II. Sensors", IEEE Transactions on Electromagnetic Compatibility, vol. EMC–25, No. 2, May 1983, pp. 107–115.

Harmuth, H. et al., "Large–Current, Short–Length Radiator for Nonsinusoidal Waves", IEEE International Symposium on Electromagnetic Compatibility, 1983, pp. 453–456.

Harmuth, H., "Introduction to Large Relative Bandwidth Radio Transmission", Antennas and Waveguides for Nonsinusoidal Waves, Academic Press, Inc., 1984, pp. 1–43.

Barrett, T., "Energy Transfer & Propagation and the Dielectrics of Materials: Transient versus Steady State Effects", Ultra–Wideband Radar—Proc. from the First Los Alamos Symposium, 1991, pp. 1–19.

Astantin, L. et al., "Ultra Wideband Signals—A New Step in Radar Development", IEEE AES Systems Magazine, Mar. 1992, pp. 12–15.

Scholtz, R., "Multiple Access with Time–Hopping Impulse Modulation", Invited paper, MILCOM 1993 Conference, Conference Record vol. 2, pp. 447–450.

Taylor, J., "Ultra–Wideband Radar Overview", Introduction to Ultra–Wideband Radar Systems, edited by J.D. Taylor, CRC Press, 1995, pp. 1–10.

Engler, Jr., H., "Technical Issues in Ultra–Wideband Radar Systems", Introduction to Ultra–Wideband Radar Systems, edited by J. D. Taylor, CRC Press, 1995, pp. 11–50.

Scholtz, R. et al., "Impulse Radio", Invited paper, IEEE PIMRC '97, Helsinki, 1997, Technical Program, Proceedings, vol. 3, pp. I–XVIII.

Bates, R., "Propagation of Transients of Currents Along Bent Wires", *Symposium Record*, IEEE International Symposium PGAP, pp. 228–234, Dec. 1966.

Lamensdorf, D., "The Transient Response of the Coaxial Cone Antenna", Sperry Research Center publication SRR-C–RR–69–42, IEEE International Symposium, PGAP, Austin, TX, Dec. 1969; also *IEEE Trans.*, AP–18, No. 6, pp. 799–802, Nov. 1970.

Susman, L. et al., "Measures of Beam Concentration for Scalar Radiation", vol. 5, No. 7, pp. 1091–1098, Jul. 1970.

Lamensdorf, D. et al., "An Analysis of Some Directive Antennas Using Time Domain Measurements", IEEE G–AP International Symposium, Los Angeles, CA, Sep. 1971.

Nicolson, A., "Broadband Microwave Transmission Characteristics from a Single Measurement of the Transient Response", *IEEE Trans. on Instrumentation and Measurement*, vol. IM–17, Dec. 4, 1968.

Hanley, G. et al., "Sinusoidal Step Response of L–Band Waveguide", *Proc. IEEE*, p. 1646, (1965).

Nicolson, A., "Wideband System Function Analyzer Employing Time to Frequency Domain Translation", presented at Wescon Convention, Session 22, San Francisco, CA, Aug. 1969.

Aukenthaler, A., Determining the Permanent of a Matrix, *PGMTT*, vol. 17, No. 10, p. 791, Oct. 1969.

Susman, L., Response of Linear Networks to Periodic Excitation, *PG–CT*, vol. CT–16, No. 4, Nov. 1969.

Nicolson, A. et al., "Comments on Applications of Time Domain Metrology to the Automation of Broadband Microwave Measurements", *IEEE Trans. on Microwave Theory & Techniques,* vol. MTT–20, p. 707, Oct. 1972.

Nicolson, A. et al., "Applications of Time Domain Metrology to the Automation of Broadband Microwave Measurements", *IEEE Trans. on PGMTT,* vol. MTT–20, No. 1, p. 3–9, Jan. 1972.

Cronson, H. et al., "Comments on Microwave Measurements by Fourier Analysis of Network Pulse Response", *Proc. IEEE,* vol. 61, pp. 1500–1501, Oct. 1973.

Cronson, H. et al., "Time Domain Measurements of Microwave Components", Electrical and Electronic Measurement & Test Instrument Conference, Ottawa, Canada, May 1973; also *IEEE Trans. Instrum. Meas.,* vol. IM–20, Dec. 1973.

Cronson, H. et al., "A 2.5ns Timing Standard", *IEEE Trans. Instrum. Meas.,* vol. IM–21, Mar. 1974.

Nicolson, A., "Forming the Fast Fourier Transform of a Step Response in Time Domain Metrology", SCRC–RP–73–19, May 1973.

Nicholson, A., Broadband Measurements on Materials Using Time–Domain Metrology, SCRC–RP–73–19, May 1993, pp. 344–347.

Cronson, H. et al., "Extensions of Time Domain Metrology Above 10 GHz to Materials Measurements", *IEEE Trans. Instrum. Meas.,* vol. IM–23, Dec. 1974.

Cronson, H., "Time Domain Metrology—An Alternative Approach to Microwave Measurements", *MicroWaves,* vol. 14, Dec. 1975, pp. 40–45.

Cronson, H., "Picosecond Pulse Sequential Waveform Generation", presented at IEEE MTT–S International Symposium, May 1975, Palo Alto, CA; published in *IEEE Trans. Microwave Th. & Tech.,* vol. MTT–23, pp. 1048–1049, Dec. 1975.

Luce, D. et al., "Time Domain Measurement of Loss and Dispersion", *IEEE Trans. Microwave Theory & Tech.,* vol. MTT–24, pp. 50–54, Jan. 1976, SCRC–RP–74–22, Jul. 1974.

Cronson, H., "A Wideband Directional Coupler for Time Domain Measurements", *IEEE Trans. on Instr. & Meas.,* vol. IM–25, pp. 15–17, Mar. 1976.

Nicolson, A. et al., "Subnanosecond Risetime Pulse Generators", *IEEE Trans. Instr. & Meas.,* vol. IM–25, pp. 104–107, Jun. 1976, SCRC–RP–74–34, Oct. 1974.

Cronson, H., "Properties of Networks and Materials in Applications of Time Domain Measurement Systems", WESCON Session 10, Sep. 1977.

Cronson, H., "Generation and Use of Composite Subnanosecond Waveforms for Measurements from 0.4 to 18 GHz", 7th European Microwave Conference, Copenhagen (Sep. 1977), pp. 566–568.

Bennett, C., et al., "Electromagnetic Pulse Response of Cylindrical Scatterers", 1968 International Antenna and Propagation Symposium, Boston, MA, Sep. 1968.

Bennett, C. et al., "Short Pulse Response of Radar Targets", 1969 International Antenna and Propagation Symposium, Austin, TX, Dec. 9–11, 1969.

Bennett, C. et al., "Transient Scattering from Conducting Cylinders", *IEEE Trans. Antennas and Propagation,* vol. AP–18, No. 5, Sep. 1970.

Bennett, C. et al., "Transient and Time Domain Solutions for Antennas and Scatterers", 1971 IEEE International Convention, New York, Mar. 1971, pp. 624–625.

Bennett, C. et al., "Transient Scattering by Three–Dimensional Conducting Surfaces with Wires", 1971 International Antenna and Propagation Symposium, Los Angeles, CA, Sep. 1971, pp. 349–351.

Auckenthaler, A. et al., "Computer Solution of Transient and Time Domain Thin–Wire Antenna Problems", IEEE Trans. Microwave Theory and Techniques, vol. MTT–10, No. 11, pp. 892–893, Nov. 1971.

Bennett, C., "The Impulse Response Augmentation Technique", 1973 International IEEE/G–AP Symposium, Boulder, CO, Aug. 1973, pp. 437–440.

Bennett, C., "Numerical Solution of Transient Electromagnetic Scattering Problems", Proc. 6th European Microwave Conference, Rome, Italy, Sep. 1976, pp. 75–80.

Toomey, J. et al., "Classification of Targets by Multifrequency Measurements", 1977 International IEEE AP–S Symposium, Palo Alto, CA, Jun. 1977, pp. 585–588.

Hieronymus, R. et al., "Space–Time Integral Equation Solution for Scattering by Cylinder with Fins", 1977 International IEEE AP–S Symposium, Palo Alto, CA, Jun. 1977, pp. 294–297.

Bennett, C., "The Numerical Solution of Transient Electromagnetic Scattering Problems", Chapter in book Electromagnetic Scattering, (ed. P. Uslenghi), Academic Press, Inc, 1978, pp. 393–428.

Fralick, S. et al., "Radiation of Electromagnetic Walsh Waves", Report to the Air Force Office of Scientific Research, Dec. 1974, pp. 1–6.

Harmuth, H., "The Dogma of the Circle", Introduction, Sequency Theory—Foundation and Applications, Academic Press, Inc., 1977, pp. 1–17.

Harmuth, H., "Frequently Raised Objections", Excerpt, Sequency Theory—Foundation and Applications, Academic Press, Inc., 1977.

Fowler, C., et al., "Assessment of Ultra–Wideband (UWB) Technology", IEEE AES Magazine, Nov. 1990, pp. 45–49.

Scholtz, R. et al., "Impulse Radio: How it works", IEEE Communications Letters, vol. 2, No. 1, Jan. 1998.

"Sampling System Application Briefs", Tek Lab Scopes, Tektronix, 1977.

Dunn, S. et al., "Signal Flow and Scattering Techniques in Microwave Network Analysis", Sperry Engineering Review, Dec. 1959, p. 10–22.

Ross, G., "Blower Delay Circuitry", Electronic Equipment Engineering, vol. 8, No. 9, Sep. 1960, pp. 54–55.

Ross, G., "Calculating the Spectrum Power Density of a Signal", Proc. IRE, vol. 48, No. 12, Dec. 1960.

Ross, G. et al., "Prediction of Coverage for Trans–Horizon HF Radar Systems", IRE Trans. on Military Electronics, vol. MIL–5, No. 2, Apr. 1961.

Ross, G., "Noise Properties of Beam Switching Tubes", Electronic Industries, vol. 20, No. 7, Jul. 1961, pp. 96–102.

Ross, G., "A Technique of Graphically Evaluating the Far Field Pattern of an Antenna", IEEE Trans. on Antennas and Propagation, vol. AP–12, No. 3, May 1964, Apr. 1964.

Ross, G., "Binary Generation of Frequencies Saves on Hardware", Electronic Design, vol. 12, No. 24, 1964, pp. 38–47.

Ross, G., "The Synthetic Generation of Phase–Coherent Microwave Signals for Transient Behavior Measurements", IEEE Trans. on Microwave Theory and Techniques, vol. MTT–13, No. 5, Sep. 1965, pp. 704–706.

Rross, G., "An Extension of the Initial Value Theorem", IEEE Trans. on Circuit Theory, vol. CT–13, No. 2, Jun. 1966, pp. 220–221.

Ross, G., "The Transient Analysis of Certain TEM Mode Four–Port Networks", IEEE Trans. on Microwave Theory and Techniques, vol. MTT–14, No. 11, Nov. 1966, pp. 528–547.

Ross, G., "A Time Domain Determination of the Driving Point Characteristics of the Dipole", Symposium Record, IEEE International Symposium on Antennas and Propagation, Dec. 1966, pp. 205–212.

Ross, G., "Choosing the Limits on the Convolution Integral", IEEE Trans. on Education, vol. #–10, No. 1, Mar. 1967, pp. 45–47.

Ross, G., "Continuous Beam Steering and Null Tracking with a Fixed Multiple–Beam Antenna Array System", IEEE Trans. on Antennas and Propagation, vol. AP–12, No. 5, Sep. 1964.

Ross, G., "A New Microwave Phase Equalizer Network", IEEE Trans. on Microwave Theory and Techniques, vol. MTT–15, No. 11, Nov. 1967, p. 647.

Ross, G., "Series and Parallel Pulse Forming Networks for the Generation of Microwave Energy", Microwave Journal, vol. 10, No. 10, Sep. 1967, p. 98.

Ross, G., "Comments on the Isolation Factor of Lossy Microstrip Couplers", IEEE Trans. on Microwave Theory and Techniques, vol. MTT–16, No. 1, Jan. 1968, p. 53.

Ross, G., "A Time Domain Criterion for the Design of Wideband Radiating Elements", IEEE Trans. on Antennas and Propagation, vol. 16, May 1968, p. 355.

Ross, G., "An Improved Pulse Forming Network for the Generation of Phase Coherent Microwave Signals", IEEE Trans. on Microwave Theory and Techniques, vol. MTT–17, 1969, p. 52.

Ross, G., "On Stored Energy and Bandwidth in TEM Mode Networks", IEEE Trans. on Microwave Theory and Techniques, vol. MTT–17, 1969, p. 386.

Ross, G., "Synchronized Microwave Energy Generation by Harmonic Filtering", IEEE Trans. on Electron Devices, vol. ED–16, 1969, p. 225.

Ross, G., "The System Function of a Microwave Dipole Aerial Derived from Time Domain Considerations", presented at the First European Microwave Conference, sponsored by IEE, IEEE and PGMTT, London, England, Sep. 1969, Symposium Record, pp. 393–396, May 1970.

Ross, G., "The Measurement of the Intrinsic Properties of Materials by Time Domain Techniques", IEEE Biennial Conference on Precision Electromagnetic Measurements, Boulder, CO, Conference Record, pp. 63–65, Jun. 4, 1970; IEEE Trans. on Instrumentation and Measurement, vol. IM–19, Nov. 1970, p. 377.

Ross, G., "A Simple Method for Obtaining the System Function of a Cascade Connection of Transmission Lines", IEEE Trans. on Microwave Theory and Techniques, vol. MTT–18, Oct. 1970, p. 738.

Ross, G., "The Generation of Pulse Modulated Signals at C Band and Beyond", IEEE Trans. on Microwave Theory and Techniques, vol. MTT–19, Jan. 1971, p. 96.

Ross, G., "The Relationship Between Risetime, Setting Time, Bandwidth and Q in Certain Distributed Microwave Networks", J. Franklin Institute, vol. 291, Jan. 1971, p. 19.

Ross, G., "A Survey of the Geophysical Applications of Subnanosecond Baseband Pulse Technology", 1971 G–AP Symposium, Sep. 1971, Symposium Record, pp. 144–145.

Ross, G., "A Balanced Antenna–Generator for the Distortionless Radiation of Subnanosecond Baseband Pulses", 1971 G–AP Symposium, Sep. 1971, Symposium Record, pp. 311–314.

Cronson, H. et al., "Current Status of Time Domain Metrology in Material and Distributed Network Research", presented at Conference on Precision Electromagnetic Measurements, Boulder, CO, Jun. 26–29, 1972.

Cronson, H. et al., Current Status of Time Domain Metrology in Material and Distributed Network Research, *IEEE Trans. on Instrumentation and Measurement*, vol. IM–21, Nov. 1972, p. 495.

Ross, G., "BARBI, A New Radar Concept for Precollision Sensing", Society of Automotive Engineers, Third International Conference on Occupant Protection, Paper No. 740574, pp. 141–152, Jul. 1974. Also presented at the Fourth European Microwave Conference, Montreux, Switzerland, Sep. 11, 1974, pp. 228–230.

Nicolson, A. et al., "A New Radar Concept for Short Range Application", IEEE 1975 International Radar Conference, Apr. 21–23, 1975, Symposium Record, pp. 146–152.

Ross, G., "The Accurate Measurement of Range by the Use of Microwave Delay Line Techniques", IEEE 1975 International Microwave Symposium, May 12–14, 1974, Symposium Record, pp. 341–343. Also *IEEE Trans. on Microwave Theory and Technique*, vol. MTT–23, Dec. 1975, pp. 1071–1074.

Ross, G., "Subnanosecond Pulse Technology and Its Applications", Plenary Invited Talk, Fifth European Microwave Symposium, Hamburg, Germany, Sep. 1975, Symposium Record, pp. 22–38.

Toevs, J. et al., "UWB Radar for Ground Vehicle Self–Protect", 1992 IEEE International Microwave Symposium, Jun. 1992.

"Ultra–Wideband Short Pulse Electromagnetics", Bertoni, H. et al., Eds. Plenum Press, 1993, pp. 167–175.

Ross, G., "Design and Construction of Subminiature IF Amplifiers", Masters Thesis, Polytechnic University, New York, Jun. 1955.

Ross, G. and A. Kraus, "Determinants and Matrices", *Electrical Manufacturing*, (Feature Article, Basic Science & Engineering series), Dec. 1959.

Ross, G., "Microwave Network Analysis", *MIT Tech. Engineering News*, 1960.

Ross, G., "The Transient Analysis of Multiple Beam Feed Networks for Array Systems", Ph.D. Thesis, Polytechnic University, New York, 1963.

Ross, G., "Phase Shifter for Wide–Band Signals", *Microwave*, vol. 6, No. 2, Mar. 1967, p. 42.

Ross, G., "Concerning the Generation of N Cycles of Phase Coherent Microwave Energy", Joint U.S.–Canadian URSI Meeting, Commission VI, Ottawa, Canada, May 23–26, 1967, Symposium Record, pp. 99–100.

Ross, G., "A Time Domain Determination of the Driving Point Properties of Certain Bent Wire Radiatiors", IEEE International Symposium on Antennas and Propagation, Ann Arbor, Michigan, Oct. 1967, Symposium Record, pp. 48–51.

Ross, G., "A New Wideband Antenna Receiving Element", 1967 NEREM Conference, Boston, MA, Nov. 1967, Symposium Record, pp. 48–51.

Ross, G., "Signal Processing Wire Antennas", *IEEE Pulse*, Polytechnic Graduate Center, Long Island, NY Presented Dec. 14, 1967.

Ross, G., "Experimental Techniques in Time Domain Scattering Ranges", *IEEE Reflector*, presented at Sylvania Research Laboratory, Waltham, MA, Feb. 13, 1968.

Ross, G., "Members of the Class of TEM Mode Wire Antennas with a TLIR", IEEE International Symposium on Antennas and Propagation, Boston, MA, Sep. 1968, Symposium Record, pp. 249–252.

Ross, G., "Picosecond Pulse Technology and Its Applications", IEEE Waves and Devices Group, Phoenix, AZ, Dec. 10, 1968.

Ross, G., "The Relationship Between Rise Time and Signal Bandwidth in Distributed Microwave Networks", IEEE Region 6 Conference, Phoenix, AZ, Apr. 1969, pp. 169–175.

Ross, G., "The State of the Art in Time Domain Electromagnetics", invited talk at the Electrical Engineering Colloquium, The City University of New York, Dec. 3, 1969.

Ross, G., "On Subnanosecond Baseband Pulse Radar", Invited IEEE G–AP Chapter Talk, Ohio State University, Nov. 17, 1971.

Ross, G. and J. DeLorenzo, "A Novel Intrusion Alarm System for Home and Industry", presented at 1972 Carnahan Conference on Electronics Crime Countermeasure, Lexington, KY, Apr. 19, 1972.

Ross, G., J. DeLorenzo and C. Bennett, "Time Domain Measurement of Microwave Absorbers", presented at Tri-Service Radar Symposium, Monterey, CA, Jun. 6–8, 1972.

Ross, G., "Time Domain Electromagnetics and Its Applications", University of Mississippi Endowed Lecture Series, Feb. 21, 1974.

Ross, G., "A Baseband Radar System for Auto Braking Applications", 1978 SAE Congress and Exposition, Cobo Hall, Mar. 21, 1978.

Ross, G., "Narrowing the Effective Beamwidth of a BAR for Auto Braking Applications", 1978 IEEE International Antennas and Propagation Society Meeting, May 18, 1978., pp. 296–301.

Ross, G. et al., Time Domain Measurements in Electromagnetics, Van Nostrand Reinholdt, New York, 1986.

Ross, G. et al., "Radar Evaluation Handbook", Artech House, 1990.

Fink et al., Electronics Engineers' Handbook, 3rd Ed, 1989, p. 14–69, "Frequency Converters and Detectors" McGraw–Hill Book Co.

Skolnick, Introduction to Radar Systems, 2d Ed., 1980, pp. 375–376, and pp. 395–396 "Detection of Radar Signals in Noise", McGraw–Hill Book Co.

Tektronix, Inc., Instruction Manual Serial No. B041072 for the Type S–2 Sampling Head, 1968, 5 pages.

Tektronix, Inc., Instruction Manual for the Type S–3 Sampling Head, 1968, pp. 33–2—33–3, 1968.

Ross, G. et al. "Early Developments and Motivations for Time–Domain Analysis and Application," *Time Domain Measurements in Electromagnetics*, Van Nostrand Reinholdt, New York, 1986, pp. 1–44.

Akimov, Y. et al., "Timing System for Ge(Li)–Detectors", *IEEE Trans. Nucl. Sci.*, NS–19, pp. 404–410 (1972).

Harmuth, H., "Range–Doppler Resolution of Electromagnetic Walsh Waves in Radar", *IEEE Trans. on Electromagnetic Compatibility*, vol. EMC–17, No. 2, May 1975, pp. 106–111.

Harmuth, H., "Antennas and Waveguides for Nonsinusoidal Waves", Academic Press, Inc., New York, 1984, pp. 1–21.

Harmuth, H., "Transmission of Information by Orthogonal Functions", Second Edition, Springer–Verlag, New York, 1972, pp. 244–291.

Harmuth, H., "Transmission of Information by Orthogonal Functions", Springer–Verlag, New York, 1969, pp. 160–180.

Harmuth, H., "Synthetic–Aperture Radar Based on Nonsinusoidal Functions: II–Pulse Compression, Contrast, Resolution, and Doppler Shift", *IEEE Trans. on Electromagnetic Compatibility,* vol. EMC–21, No. 1, Feb. 1979, pp. 40–49.

Harmuth, H., "Synthetic–Aperture Radar Based on Nonsinusoidal Functions: IV–Pulse–Position and Pulse–Shape Coding", *IEEE Trans. on Electromagnetic Compatibility,* vol. EMC–22, No. 2, May 1980, pp. 93–106.

Young, J., "Radar Imaging from Ramp Response Signatures", *IEEE Trans. on Antennas and Propagation,* vol. AP–24, No. 3, May 1976, pp. 276–282.

Baum, C., "Emerging Technology for Transient and Broad–Band Analysis and Synthesis of Antennas and Scatterers", *Proc. of the IEEE,* vol. 64, No. 11, Nov. 1976, pp. 1598–1617.

Kennaugh, E. et al., "Transient and Impulse Response Approximations", *Proc. of the IEEE,* Aug. 1965, pp. 893–901.

Scott, William B., "UWB Technologies Show Potential For High–Speed, Covert Communications", [*Aviation Week & Space Technology*], 40, 44, (Jun. 4, 1990).

Scott, William B., "Defense Dept. Panel of Radar Experts To Study Ultra–Wideband Technologies", [*Aviation Week & Space Technology*], 55, (Mar. 26, 1990).

Bennett, Leonard C. et al., "Time–Domain Electromagnetics and Its Applications" [*Proceedings of the IEEE*], 66, 3, 299–316 (Mar. 3, 1978).

Anderson, Forrest et al., "Wideband Beam Patterns from Sparse Arrays" [*Proceedings of the First Los Alamos Symposium*], 273–286.

Bretthorst, G. Larry, "Radar Target Discrimination Using Probability Theory" [*Proceedings of the First Los Alamos Symposium*], 417–434.

"Pulse and Waveform Generation with Step Recovery Diodes", Hewlett Packard Application Note 918, Hewlett–Packard, Jun. 1986, pp. 1–22.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20 is confirmed.

New claims 21–49 are added and determined to be patentable.

21. The radar motion sensor of claim 1, wherein the receiver has a sensitivity to detect reflections of a transmitted signal from a reflecting body at a range of 1–12 feet from the receiver antenna.

22. The radar motion sensor of claim 1, wherein the transmit antenna and the receiver antenna comprise a shared element.

23. The radar motion sensor of claim 1, wherein the transmit pulse generator, gating pulse generator and UWB radar receiver, comprise elements operating with a maximum power supply voltage of 6 volts.

24. The radar motion sensor of claim 1, wherein the pulse repetition interval generator, fixed reference delay means, transmit pulse generator, adjustable delay means, gating pulse generator, UWB radar receiver, and signal processing means comprise elements operating with a maximum power supply voltage of 6 volts.

25. The radar motion sensor of claim 1, including a penlight battery supplying power to the pulse repetition interval generator, fixed reference delay means, transmit pulse generator, adjustable delay means, gating pulse generator, UWB radar receiver, and signal processing means.

26. An ultra-wideband (UWB) radar motion sensor, comprising:
    a pulse repetition interval generator;
    a fixed reference delay means connected to the pulse repetition interval generator;
    a transmit pulse generator connected to the reference delay means;
    a transmit antenna connected to the transmit pulse generator;
    an adjustable delay means connected to the pulse repetition interval generator;
    a gating pulse generator connected to the adjustable delay means;
    an UWB radar receiver connected to the gating pulse generator;
    a receiver antenna connected to the UWB receiver; and
    signal processing means connected to the UWB receiver; wherein the UWB receiver includes a sampler which accumulates effects of a plurality of signals on the receiver antenna in response to a corresponding plurality of gating pulses generated by the gating pulse generator to produce a sampler signal.

27. The radar motion sensor of claim 26, wherein said effects comprise respective sums of signals on the receiver antenna and corresponding gating pulses which exceed a diode threshold.

28. The radar motion sensor of claim 26, wherein the sampler comprises a capacitor having one terminal connected to the receive antenna, a diode having a first terminal coupled to another terminal of the capacitor, and having a second terminal coupled to the gating pulse generator.

29. The radar motion sensor of claim 28, wherein the sampler comprises an analog amplifier having an input coupled to the first terminal of the diode.

30. An ultra-wideband (UWB) radar motion sensor, comprising:
    a pulse repetition interval generator;
    a fixed reference delay means connected to the pulse repetition interval generator;
    a transmit pulse generator connected to the reference delay means;
    a transmit antenna connected to the transmit pulse generator;
    an adjustable delay means connected to the pulse repetition interval generator;
    a gating pulse generator connected to the adjustable delay means;
    an UWB radar receiver connected to the gating pulse generator;
    a receiver antenna connected to the UWB receiver; and
    signal processing means connected to the UWB receiver; wherein the transmit pulse generator comprises circuitry biased for operation in a non-avalanche mode which supplies a transmit pulse to the transmit antenna.

31. The radar motion sensor of claim 30, wherein the circuitry biased for operation in a non-avalanche mode comprises a step recovery diode.

32. The radar motion sensor of claim 30, wherein the circuitry biased for operation in a non-avalanche mode comprises a bipolar transistor.

33. An ultra-wideband (UWB) radar motion sensor, comprising:
    a pulse repetition interval generator;
    a fixed reference delay means connected to the pulse repetition interval generator;
    a transmit pulse generator connected to the reference delay means;
    a transmit antenna connected to the transmit pulse generator;
    an adjustable delay means connected to the pulse repetition interval generator;
    a gating pulse generator connected to the adjustable delay means;
    an UWB radar receiver connected to the gating pulse generator;
    a receiver antenna connected to the UWB receiver; and
    signal processing means connected to the UWB receiver; wherein the receiver comprises an integrating sampler.

34. An ultra-wideband (UWB) radar motion sensor, comprising:
    a pulse repetition interval generator;
    a fixed reference delay means connected to the pulse repetition interval generator;
    a transmit pulse generator connected to the reference delay means;
    a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver; wherein the receiver comprises a differential integrating sampler.

35. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver; wherein the receiver comprises an integrating sampler, and the signal processing means comprises an integrator which smooths the output of the integrating sampler, and a differentiator which differentiates the output of the integrator to obtain target motion information.

36. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pule repetition interval generator;

a gating pulse generator connected to the adjustable delay means;

an UWB radar receiver connected to the gating pulse generator;

a receiver antenna connected to the UWB receiver; and signal processing means connected to the UWB receiver; wherein the transmit pulse generator comprises a circuit producing antenna ringdown pulses on the transmit antenna.

37. The motion detector of claim 36, wherein the UWB radar receiver comprises an integrating sampler.

38. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver; wherein UWB receiver includes resources to receive return echoes for a plurality of ranges, including a first range and a second range different than the first range.

39. The radar motion sensor of claim 38, wherein the signal processing means determines target velocity in response to the received return echoes for the first and second ranges.

40. The radar motion sensor of claim 38, wherein the UWB receiver comprises an integrating sampler, and resources to time multiplex use of the integrating sampler for the first and second range.

41. The radar motion sensor of claim 38, wherein the UWB receiver comprises a plurality of integrating samplers for the plurality of ranges respectively.

42. The radar motion sensor of claim 38, wherein the UWB receiver comprises a first integrating sampler and second integrating sampler, and a circuit to delay arrival of gating pulses from the gate pulse generator to the second integrating sampler relative to arrival of gating pulses from the gate pulse generator to the first integrating sampler.

43. The radar motion sensor of claim 38, wherein the UWB receiver comprises a first integrating sampler and second integrating sampler, and a circuit to delay arrival of signals from the receive antenna to the second integrating sampler relative to arrival of signals from the receive antenna to the first integrating sampler.

44. The radar motion sensor of claim 38, wherein the transmit pulse generator comprises a circuit producing antenna ringdown pulses on the transmit antenna.

45. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver; wherein the receiver comprises an input node coupled to the receive antenna, a diode having an anode and a cathode, the anode coupled to the input node, and the cathode coupled to the gating pulse generator, a capacitive node coupled to the anode of the diode at which effects of a plurality of pulses accumulate.

46. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver;

wherein the receiver comprises:

an first input node coupled to the receive antenna, a first diode having an anode and a cathode, the anode coupled to the first input node, and the cathode coupled to the gating pulse generator, a first capacitive node coupled to the anode of the diode at which a first signal reflecting effects of a plurality of pulses accumulate;

an second input node coupled to the receive antenna, a second diode having an anode coupled to the second input node and a cathode coupled to the gating pulse generator, a second capacitive node coupled to the anode of the second diode at which a second signal reflecting effects of a plurality of pulses accumulate; and a circuit to combine the first signal and the second signal produce a receiver output.

47. An ultra-wideband (UWB) radar motion sensor, comprising:

a pulse repetition interval generator;

a fixed reference delay means connected to the pulse repetition interval generator;

a transmit pulse generator connected to the reference delay means;

a transmit antenna connected to the transmit pulse generator;

an adjustable delay means connected to the pulse repetition interval generator;

a gating pulse generator connected to the adjustable delay means;

an UWB radar receiver connected to the gating pulse generator;

a receiver antenna connected to the UWB receiver; and signal processing means connected to the UWB receiver;

wherein the pulse repetition interval generator, fixed reference delay means, transmit pulse generator, adjustable delay means, gating pulse generator, UWB radar receiver, and signal processing means comprise elements on a single integrated circuit.

48. The radar motion sensor of claim 47, wherein the integrated circuit comprises a silicon integrated circuit.

49. An ultra-wideband (UWB) radar motion sensor, comprising:

a pulse repetition interval generator;

a fixed reference delay means connected to the pulse repetition interval generator;

a transformerless transmit pulse generator connected to the reference delay means;

a transmit antenna connected to the transmit pulse generator;

an adjustable delay means connected to the pulse repetition interval generator;

a gating pulse generator connected to the adjustable delay means;

an inductorless UWB radar receiver connected to the gating pulse generator;

a receiver antenna connected to the UWB receiver; and signal processing means connected to the UWB receiver.

* * * * *